United States Patent [19]

Macielag et al.

[11] Patent Number: 5,470,830
[45] Date of Patent: Nov. 28, 1995

[54] MOTILIN-LIKE POLYPEPTIDES THAT INHIBIT GASTROINTESTINAL MOTOR ACTIVITY

[75] Inventors: Mark J. Macielag, Branchburg; Ramalinga Dharanipragada, Chatham; Mary S. Marvin, Morristown, all of N.J.

[73] Assignee: Ohmeda Pharmaceutical Products Division Inc., Liberty Corner, N.J.

[21] Appl. No.: 103,489

[22] Filed: Aug. 6, 1993

[51] Int. Cl.$^6$ .............................. A61K 38/00; C07K 5/00; C07K 7/00; C07K 17/00
[52] U.S. Cl. .............................. 514/13; 514/14; 530/326; 530/327
[58] Field of Search .............................. 530/326, 327; 514/13, 14

[56] References Cited

FOREIGN PATENT DOCUMENTS

| 1355720 | 8/1989 | European Pat. Off. . |
| 1378078 | 1/1990 | European Pat. Off. . |
| 0378078 | 7/1990 | European Pat. Off. . |
| 2507573 | 4/1992 | European Pat. Off. . |

OTHER PUBLICATIONS

Peeters et al Peptides vol. 13 p. 1103 (Nov./1992).
Meyer et al, Medizinische Klinik vol. 86 p. 515 (1991).
Peeters et al. Biomedical Research vol. 9, p. 361 (1988).
Chemical Abstract, vol. 112, No. 11, (Mar. 12, 1990), p. 240; Abst. #93249g.
Chemical Abstract, vol. 115, No. 11, (Sep. 16, 1991), p. 76; Abst #106013q.

Primary Examiner—Jill Warden
Assistant Examiner—Sheela J. Huff
Attorney, Agent, or Firm—R. Hain Swope; Larry R. Cassett

[57] ABSTRACT

This invention pertains to polypeptides having gastrointestinal motor inhibitory activity represented by the formula:

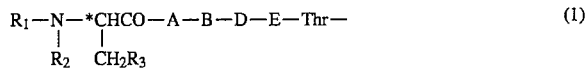

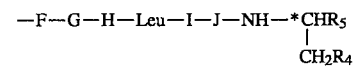

including optically active isomeric forms and the pharmaceutically acceptable acid addition salts thereof wherein A is the L-stereoisomer of a lipophilic aliphatic or alicyclic amino acid; B is selected from the group consisting of L and D aromatic, heteroaromatic, lipophilic aliphatic, and alicyclic amino acids; D is the L-stereoisomer of a lipophilic aliphatic or alicyclic amino acid; E is the L-stereoisomer of an aromatic, aliphatic, or alicyclic amino acid; F is the L-stereoisomer of an aromatic or heteroaromatic amino acid; G is glycine or D-alanine; H is L-glutamic acid or L-glutamine; I is L-glutamine, L-glutamic acid, or L-alanine; J is a direct bond between I and group —NH— or is selected from the group consisting of Z, Z-Leu, Z-Leu-Gln, Z-Leu-Gln-Glu (SEQ ID NO:2), Z-Leu-Gln-Glu-Lys (SEQ ID NO:3), Zleu-Gln-Glu-Lys-Glu (SEQ ID NO:4), Z-Leu-Gln-Glu-Lys-Glu-Arg (SEQ ID NO:5), ZLeu-Gln-Glu-Lys-Glu-Arg-Asn (SEQ ID NO:6), Z-Leu-Gln-Glu-Lys-Glu-Arg-AsnLys (SEQ ID NO:7), and Z-Leu-Gln-Glu-Lys-Glu-Arg-Asn-Lys-Gly (SEQ ID NO:8), wherein Z is selected from the group consisting of arginine, D-arginine, D-homoarginine, D-lysine, D-ornithine, D-2,4-diaminobutyric acid, D-glutamine, D-asparagine, and D-alanine; $R_1$ and $R_2$ are independently hydrogen or lower alkyl; $R_3$ is selected from the group consisting of lower-alkyl, cycloalkyl, substituted and unsubstituted aryl, and heteroaryl, wherein the aryl group may be substituted with one or more substituents selected from the group consisting of halogen, hydroxy, and lower-alkoxy; $R_4$ is selected from the group consisting of —CH$_2$CONH$_2$, aminoalkyl groups containing from 1 to 3 carbon atoms, and guanidinoalkyl groups containing 2 or 3 carbon atoms; $R_5$ is —COOH or —CONH$_2$; and the symbol * represents an asymmetric carbon atom which may be in the D or L configuration, and each lower-alkyl group contains from 1 to 4 carbon atoms, with the proviso that $R_4$ is —CH$_2$CONH$_2$ only when J is Z-Leu or Z-Leu-Gln-Glu-Lys-Glu-Arg-Asn-Lys-Gly (SEQ ID NO:8).

19 Claims, No Drawings

MOTILIN-LIKE POLYPEPTIDES THAT INHIBIT GASTROINTESTINAL MOTOR ACTIVITY

FIELD OF THE INVENTION

This invention relates to novel polypeptides having potent gastrointestinal motor inhibitory activity useful in the treatment of conditions characterized by elevated plasma motilin levels such as infectious diarrhea and Crohn's disease.

BACKGROUND OF THE INVENTION

Motilin is a gastrointestinal linear polypeptide hormone which stimulates the gastric antrum, duodenum, and colon. Although its effects are not completely known, motilin plays a role in increasing gastric motility and stimulating pepsin output and may also be important in regulating the interdigestive myoelectric complex. Human motilin has not yet been purified, but its immunologic properties strongly suggest that it is very similar to porcine motilin. Porcine motilin contains amino acid residues and may be represented by the formula:

```
                          10                          20                    SEQ ID NO:1
H—Phe—Val—Pro—Ile—Phe—Thr—Tyr—Gly—Glu—Leu—Gln—Arg—Met—Gln—Glu—Lys—Glu—Arg—Asn—Lys—Gly—Gln—OH
```

Porcine motilin has a hydrophobic region from positions 1 to 5, a hydrophilic region from positions 11 to 22, and a connecting region from positions 6 to 10. Porcine motilin also has an α-helical secondary structure from residues 9 to 20 of the primary sequence [Khan et al., *Biochemistry* 29, 5743–5751 (1990)].

Administration of motilin to healthy human subjects accelerates intestinal transit time and enhances gastric emptying. In vitro, motilin stimulates contractions of human and rabbit duodenal smooth muscle strips and isolated gastrointestinal smooth muscle cells. In addition, motilin and some of its derivatives compete with radiolabelled motilin for binding sites on human and rabbit antral tissue suggesting that stimulation of specific receptors in the gastrointestinal tract is responsible for the physiological effects of the hormone. Infusion of motilin has been reported to stimulate the emptying of solids and liquids in patients with diabetic gastroparesis [Peeters et al., *Gastroenterology* 100, A480 (1991)]. In addition, motilin has been used to treat patients with paralytic ileus caused by carcinoma of the gastrointestinal tract [Meyer et al., *Med. Klin.* 86, 515– 517 (1991)]. Motilin has a relatively short half-life ($t_{1/2}$) of 4.5 minutes in humans, Christofides et al., *Gastroenterology* 76, 903–907(1979), which makes it necessary to administer the hormone by continuous infusion to induce a therapeutic effect.

The N-terminal amino acid sequence and certain residues of the mid-portion of motilin are essential for contractile activity, [Macielag et al., *Peptides* 13, 565–569 (1992); Peeters et al., *Peptides* 13, 1103–1107 (1992); Poitras et al., *Biochem. Biophys. Res. Commun.* 183, 36–40 (1992)]. Motilin-like polypeptides which have a shorter C-terminus, contain from 3 to 5 basic amino acids bonded from position 12, and have various amino acid substitutions at positions 1 through 11 have been reported to have activity less than, or equal to, that of motilin.

A motilin antagonist which displaces labeled porcine motilin in rabbit smooth muscle has been reported, "The Motilin Antagonist ANQ-11125 Blocks Erythromycin-induced Contractions In Vitro", Peeters, T. L., Depoortere, I., Macielag, M. J., Dharanipragada, R., Marvin, M. S., Florance, J. R., Vantrappen, G., Galdes, A., *Gastroenterology* 1993, 104, A564.

Although a clear correlation has not been established between hypermotilinemia and disease, elevated plasma motilin levels have been observed in clinical conditions associated with gastrointestinal hypermotility syndromes such as infectious diarrhea and Crohn's disease. This observation suggests that an agent which inhibits the interaction of motilin with its receptor would be useful in the treatment of the disordered intestinal peristalsis associated with these conditions.

In addition, a motilin-like polypeptide having potent gastrointestinal motor inhibitory activity would be useful for the treatment of increased basal levels of gastrointestinal motor activity.

SUMMARY OF THE INVENTION

This invention pertains to polypeptides having gastrointestinal motor inhibitory activity represented by the formula:

$$R_1-N-*CHCO-A-B-D-E-Thr- \quad (1)$$
$$\underset{R_2}{|} \underset{CH_2R_3}{|}$$

$$-F-G-H-Leu-I-J-NH-*CHR_5$$
$$\underset{CH_2R_4}{|}$$

including optically active isomeric forms and the pharmaceutically acceptable acid addition salts thereof wherein:

A is the L-stereoisomer of a lipophilic aliphatic or alicyclic amino acid;

B is selected from the group consisting of L and D aromatic, heteroaromatic, lipophilic aliphatic, and alicyclic amino acids;

D is the L-stereoisomer of a lipophilic aliphatic or alicyclic amino acid;

E is the L-stereoisomer of an aromatic, aliphatic, or alicyclic amino acid;

F is the L-stereoisomer of an aromatic or heteroaromatic amino acid;

G is glycine or D-alanine;

H is L-glutamic acid or L-glutamine;

I is L-glutamine, L-glutamic acid, or L-alanine;

J is a direct bond between I and group —NH— or is selected from the group consisting of Z, Z-Leu, Z-Leu-Gln, Z-Leu-Gln-Glu, (SEQ ID NO:2), Z-Leu-Gln-GluLys (SEQ ID NO:3), Z-Leu-Gln-Glu-Lys-Glu (SEQ ID NO:4), Z-Leu-Gln-Glu-Lys-GluArg (SEQ ID NO:5), Z-Leu-Gln-Glu-Lys-Glu-Arg-Asn (SEQ ID NO:6), Z-Leu-GlnGlu-Lys-Glu-Arg-Asn-Lys (SEQ ID NO:7), and Z-Leu-Gln-Glu-Lys-Glu-Arg-AsnLys-Gly (SEQ ID NO:8), wherein Z is selected from the group consisting of arginine. D-arginine, D-homoarginine, D-lysine, D-ornithine, D-2,4-diaminobutyric acid, Dglutamine, D-asparagine, and D-alanine;

$R_1$ and $R_2$ are independently hydrogen or lower-alkyl;

$R_3$ is selected from the group consisting of lower-alkyl, cycloalkyl, substituted and unsubstituted aryl, and heteroaryl, wherein the aryl group may be substituted with one or more substituents selected from the group consisting of halogen, hydroxy, and lower-alkoxy;

$R_4$ is selected from the group consisting of —$CH_2CONH_2$, aminoalkyl groups containing from 1 to 3 carbon atoms, and guanidinoalkyl groups containing 2 or 3 carbon atoms;

$R_5$ is —COOH or —$CONH_2$; and the symbol * represents an asymmetric carbon atom which may be in the D or L configuration, and each lower-alkyl group contains from 1 to 4 carbon atoms, with the proviso that $R_4$ is —$CH_2CONH_2$ only when J is Z-Leu or Z-Leu-Gln-Glu-Lys-Glu-Arg-Asn-Lys-Gly (SEQ ID NO:8).

DETAILED DESCRIPTION OF THE INVENTION

The novel polypeptides of the present invention are distinct from motilin and yet inhibit the interaction of motilin with its receptor thereby preventing the peristaltic effects of the hormone on gastrointestinal tissue. The motilin-like polypeptides contain an aromatic, heteroaromatic, lipophilic aliphatic, or alicyclic amino acid residue, which is preferably D-phenylalanine or L-phenylalanine, in place of proline at position 3 to inhibit the interaction of motilin with its receptor. The polypeptides of the present invention are therefore useful as investigative tools for probing membrane-bound motilin receptors and are useful in the treatment of conditions characterized by a increased basal level of gastrointestinal motor activity such as infectious diarrhea and Crohn's disease.

This invention pertains to novel polypeptides having potent gastrointestinal motor inhibitory activity as well as to methods for treating a condition of increased basal level of gastrointestinal motor activity in a mammal, particularly a human. The methods comprise administering to the mammal an amount, therapeutically effective to relieve such condition, of a polypeptide represented by formula (1):

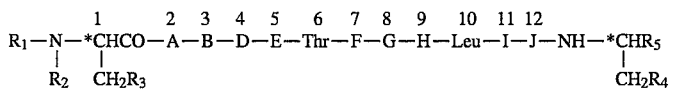

(1)

including optically active isomeric forms and the pharmaceutically acceptable acid. In formula (1), the symbol * represents an asymmetric carbon atom which may be in the D or L configuration, and each lower-alkyl group contains from 1 to 4 carbon atoms, providing that R4 is —$CH_2CONH_2$ only when J is Z-Leu or Z-Leu-Gln-Glu-Lys-Glu-Arg-Asn-Lys-Gly (SEQ ID NO:8). $R_1$ through $R_5$ are defined as set forth below.

The novel compounds of the present invention defined by Formula (1) are polypeptides which may be from 12 to 22 amino acids in length, and preferably are 12, 14, 16, 18, 20, or 22 amino acids in length. The stereochemistry of the constituent amino acids of the novel polypeptides is an essential feature of this invention. The absolute stereochemistry of the individual amino acids is L, unless otherwise noted, except for position 1 (the amino-terminal amino acid, $R_1)(R_2)N$—*$CH(CH_2R_3)CO$—) which may be L or D, position 3 (Group B) which may be of L or D, position 8 (Group G) which may be glycine or D-alanine, position 12 which may be L or D, and the C-terminal amino acid position, —NH—*$CH(CH_2R_4)R_5$, which may be L or D.

The following abbreviations employed throughout this specification are defined as set forth below:
Phe—phenylalanine
Tyr—tyrosine
Nle—norleucine
Leu—leucine
Cha—β-cyclohexylalanine
Val—valine
Ile—isoleucine
Gly—glycine
Ala—alanine
Glu—glutamic acid
Gln—glutamine
Arg—arginine
h-Arg—homoarginine
Orc—ornithine
Dab—2,4-diaminobutyric acid
Lys—lysine
Ash—asparagine
Me—methyl
Boc—t-butyloxycarbonyl
Cbz—benzyloxycarbonyl
Dhbt—3,4-dihydro-4-oxobenzotriazin-3-yl
Fmoc—fluorenylmethyloxycarbonyl
Mbh—4,4'-dimethoxybenzhydryl
Mtr—4-methoxy-2,3,6-trimethylbenzenesulfonyl
Pfp—pentafluorophenyl
Trt—trityl
BOP—benzotriazolyloxy-trisdimethylaminophosphonium hexafluorophosphate
DCC—N',N'-dicyclohexylcarbodiimide
DCM—dichloromethane
DIC—diisopropylcarbodiimide
DIEA—diisopropylethylamine
EDCC—N-diethylaminopropyl-N'-cyclohexylcarbodiimide
HBTU—2-(1H-benzotriazol-1-yl)-1,1,3,3-tetramethyluronium hexafluorophosphate
HEPES—(N-[2-hydroxyethyl]piperazine-N'-[2-ethanesulfonic acid])
HMPA—hydroxymethylphenoxyacetoxy
HOBt—1-hydroxybenzotriazole
MBHA—4-methylbenzhydrylamino
PAM—hydroxymethylphenylacetamidomethyl PyBrOP—bromo-tris-pyrrolidino-phosphonium hexafluorophosphate
DMF—N,N-dimethylformamide
NMM—N-methylmorpholine
NMP—N-methylpyrrolidinone
TCA—trichloroacetic acid
TEA—triethylamine
TFA—trifluoroacetic acid
TFMSA—trifluoromethanesulfonic acid Position 1, the Amino-Terminal Amino Acid,
$(R_1)(R_2)N$—*$CH(CH_2R_3)CO$—

The amino acid in the amino-terminal portion of the polypeptide, $(R_1)(R_2)N$—*$CH(CH_2R_3)CO$—, in position 1 may have the L or D configuration. $R_1$ and $R_2$ may be independently selected from the group consisting of hydrogen and lower-alkyl. The amino-terminal portion may be unsubstituted, in which case $R_1$ and $R_2$ are hydrogen. The term "lower-alkyl", as used herein, refers to straight- and branched-chain hydrocarbon radicals containing from 1 to 4 carbon atoms. Examples of suitable lower-alkyl groups for $R_1$ and $R_2$ are methyl, ethyl, propyl, isopropyl, butyl, isobutyl, and sec-butyl, preferably methyl. Preferably, the amino-terminal amino acid is N-substituted, and the preferred substituents are one or two methyl groups.

$R_3$ is selected from the group consisting of lower-alkyl, cycloalkyl, substituted and unsubstituted aryl, and heteroaryl, wherein the aryl group may contain one or more substituents selected from the group consisting of halogen, hydroxy, and lower-alkoxy. Preferred substituted and unsubstituted aryl groups are phenyl, p-fluorophenyl, p-chlorophenyl, p-bromophenyl, p-iodophenyl, p-hydroxyphenyl, p-methoxyphenyl, 1-naphthyl, and 2-naphthyl. Preferred heteroaryl groups are 3-indolyl, 2-thienyl, and 3-pyridyl. Preferred cycloalkyl groups are cyclopentyl, cyclohexyl, and cycloheptyl. Preferably, $R_3$ is selected from the group consisting of methyl, ethyl, n-propyl, iso-propyl, n-butyl, cyclohexyl, phenyl, p-fluorophenyl, p-chlorophenyl, p-bromophenyl, p-iodophenyl, p-hydroxyphenyl, p-methoxyphenyl, 1-naphthyl, 2-naphthyl, 3-indolyl, 2-thienyl, and 3-pyridyl. More preferably, $R_3$ is selected from the group consisting of phenyl and cyclohexyl. Examples of the amino acid residues from which $(R_1)(R_2)N-*CH(CH_2R_3)CO-$ may be derived are phenylalanine, p-fluorophenylalanine, p-chlorophenylalanine, p-bromophenylalanine, p-iodophenylalanine, tyrosine, p-methoxyphenylalanine, 1-naphthylalanine. 2-naphthylalanine, tryptophan, β-2-thienylalanine, β-3-pyridylalanine, α-aminobutyric acid, norvaline, norleucine, leucine, and cyclohexylalanine. For compounds having high levels of gastrointestinal antiperistaltic activity, the preferred amino-terminal amino acids are L-phenylalanine, D-phenylalanine, L-cyclohexylalanine, and D-cyclohexylalanine.

Position 2, Group A

Group A in position 2 of the polypeptide is an amino acid which is the L-stereoisomer of a lipophilic aliphatic or alicyclic amino acid such as valine, isoleucine, leucine, norvaline, norleucine, and cyclohexylalanine. The preferred Group A amino acids are L-valine, L-leucine, and L-isoleucine.

Position 3, Group B

Group B in position 3 is an amino acid which may be of the L or D configuration and is any of several aromatic, heteroaromatic, lipophilic aliphatic, and alicyclic amino acid residues. These amino acid residues may be derived from the group including phenylalanine, p-fluorophenylalanine, p-chlorophenylalanine, p-bromophenylalanine, p-iodophenylalanine, tyrosine, p-methoxyphenylalanine, 1 -naphthylalanine, 2-naphthylalanine, tryptophan, β-2-thienylalanine, β-3pyridylalanine, α-aminobutyric acid, norvaline, norleucine, leucine, and cyclohexylalanine. For compounds having high levels of motilin receptor antagonist activity, the preferred Group B amino acids are D-phenylalanine and L-phenylalanine. In the definition of Group B, proline and alanine are not included within lipophilic aliphatic amino acids. Proline and alanine in position 3 do not yield polypeptides having antagonist activity.

Position 4, Group D

Group D in position 4 is an amino acid which is the L-stereoisomer of a lipophilic aliphatic or alicyclic amino acid such as isoleucine, valine, leucine, norvaline, norleucine, and cyclohexylalanine. The preferred Group D amino acids are L-isoleucine, L-leucine, and L-cyclohexylalanine.

Position 5, Group E

Group E in position 5 is an amino acid which is the L-stereoisomer of an aromatic, aliphatic, or alicyclic amino acid such as phenylalanine, p-fluorophenylalanine, p-chlorophenylalanine, p-bromophenylalanine, p-iodophenylalanine, tyrosine, p-methoxyphenylalanine, 1-naphthylalanine, 2-naphthylalanine, leucine, alanine, and cyclohexylalanine. The preferred Group E amino acids are L-phenylalanine, L-alanine, and L-cyclohexylalanine.

Position 6, L-threonine

The amino acid in position 6 is L-threonine.

Position 7, Group F

Group F in position 7 is an amino acid which is the L-stereoisomer of an aromatic or heteroaromatic amino acid such as tyrosine, phenylalanine, p-methoxyphenylalanine, histidine, tryptophan, β-2-thienylalanine, and β-3pyridylalanine. The preferred Group F amino acids are L-tyrosine, L-histidine, and L-phenylalanine.

Position 8, Group G

Group G in position 8 is an amino acid which is glycine or D-alanine, preferably glycine.

Position 9, Group H

Group H in position 9 is an amino acid which L-glutamic acid or L-glutamine, preferably L-glutamic acid.

Position 10, L-leucine

The amino acid in position 10 is L-leucine.

Position 11, Group I

Group I in position 11 is an amino acid which is L-glutamine, L-glutamic acid, or L-alanine, preferably L-glutamine and L-alanine.

Group J

Group J may be a direct bond between Group I and the —NH— group or may be selected from the group consisting of Z, Z-Leu, Z-Leu-Gln, Z-Leu-Gln-Glu (SEQ ID NO:2), Z-Leu-Gln-Glu-Lys (SEQ ID NO:3), Z-Leu-Gln-Glu-Lys-Glu (SEQ ID NO:4), Z-Leu-Gln-Glu-Lys-Glu-Arg (SEQ ID NO:5), Z-Leu-Gln-Glu-Lys-GluArg-Asn (SEQ ID NO:6), Z-Leu-Gln-Gl⁻¹-Lys-Glu-Arg-Asn-Lys (SEQ ID NO:7), and Z-Leu-Gln-Glu-Lys-Glu-Arg-Asn-Lys-Gly (SEQ ID NO:8), and preferably from the group consisting of Z-Leu, Z-Leu-Gln-Glu (SEQ ID NO:2), Z-Leu-Gln-Glu-Lys-Glu (SEQ ID NO:4), Z-Leu-Gln-Glu-Lys-Glu-Arg-Asn (SEQ ID NO:6), and Z-Leu-Gln-GluLys-Glu-Arg-Asn-Lys-Gly (SEQ ID NO:8).

Position 12

When Group J is a direct bond between Group I and the —NH— group, the polypeptide is a dodecapeptide and the amino acid in position 12 is the C-terminal portion, —NH—*CH(CH$_2$R$_4$)—R$_5$, of the polypeptide wherein $R_4$ is an aminoalkyl group containing from 1 to 3 carbon atoms or a guanidinoalkyl group containing 2 or 3 carbon atoms, preferably the latter. Preferred aminoalkyl groups are aminomethyl, 2-aminoethyl, and 3-amino-n-propyl. Preferred guanidinoalkyl groups are N-2-guanidinoethyl and N-3- guanidino-n-propyl. Group $R_5$ is —COOH or —CONH$_2$, preferably —CONH$_2$. Preferably, the amino acid in the C-terminal portion, —NH*CH(CH$_2$R$_4$)—R$_5$, of the polypeptide in this embodiment is selected from the group consisting of arginine, D-arginine, lysine, D-lysine, D-ornithine, D- 2,4-diaminobutyric acid, and D-homoarginine, and more preferably is selected from the group consisting of arginine, D-arginine, lysine, and D-lysine.

When Group J is not a direct bond between Group I and the —NH— group, the amino acid in position 12 is Group Z, as defined above.

Position 13

When the polypeptide in the present invention is a tridecapeptide, the amino acid in position 13 is the C-terminal portion. —NH—*CH(CH$_2$R$_4$)—R$_5$, of the polypeptide, may have the L or D configuration, and may be selected from the group consisting of lysine, ornithine, 2,4-diaminobutyric acid, arginine, and homoarginine, preferably L-lysine or D-lysine.

When the polypeptide of the present invention is larger than a tridecapeptide, the amino acid in position 13 is L-leucine.

Position 14

When the polypeptide in the present invention is a tetradecapeptide, the amino acid in position 14 is the C-terminal portion, —NH—*CH(CH$_2$R$_4$)—R$_5$, of the polypeptide, may have the L or D configuration, and may be selected from the group consisting of glutamine, lysine, ornithine, 2,4-diaminobutyric acid, arginine, and homoarginine, and preferably is selected from the group consisting of L-lysine, D-lysine, L-glutamine, and D-glutamine.

When the polypeptide of the present invention is larger than a tetradecapeptide, the amino acid in position 14 of the polypeptide is L-glutamine.

Position 15

When the polypeptide is a pentadecapeptide, the amino acid in position 15 is the C-terminal portion, —NH—*CH(CH$_2$R$_4$)—R$_5$, of the polypeptide, may have the L or D configuration, and may be selected from the group consisting of lysine, ornithine, 2,4-diaminobutyric acid, arginine, and homoarginine, preferably L-lysine or D-lysine.

When the polypeptide of the present invention is larger than a pentadecapeptide, the amino acid in position 15 is L-glutamic acid.

Position 16

When the polypeptide is a hexadecapeptide, the amino acid in position 16 is the C-terminal portion, —NH—*CH(CH$_2$R$_4$)—R$_5$, of the polypeptide, may have the L or D configuration, and may be selected from the group consisting of lysine, ornithine, 2,4-diaminobutyric acid, arginine, and homoarginine, preferably L-lysine or D-lysine.

When the polypeptide of the present invention is larger than hexadecapeptide, the amino acid in position 16 of the polypeptide is L-lysine.

Position 17

When the polypeptide is a heptadecapeptide, the amino acid in position 17 is the C-terminal portion, —NH—*CH(CH$_2$R$_4$)—R$_5$, of the polypeptide, may have the L or D configuration, and may be selected from the group consisting of lysine, ornithine, 2,4-diaminobutyric acid, arginine, and homoarginine, preferably L-lysine or D-lysine.

When the polypeptide of the present invention is larger than a heptadecapeptide, the amino acid in position 17 is L-glutamic acid.

Position 18

When the polypeptide is an octadecapeptide, the amino acid in position 18 is the C-terminal portion, —NH—*CH(CH$_2$R$_4$)—R$_5$, of the polypeptide, may have the L or D configuration, and may be selected from the group consisting of lysine, ornithine, 2,4-diaminobutyric acid, arginine, and homoarginine, and preferably is selected from the group consisting of L-lysine, D-lysine, L-arginine, and D-arginine.

When the polypeptide of the present invention is larger than an octadecapeptide, the amino acid in position 18 of the polypeptide is L-arginine.

Position 19

When the polypeptide is a nonadecapeptide, the amino acid in position 19 is the C-terminal portion, —NH—*CH(CH$_2$R$_4$)—R$_5$, of the polypeptide, may have the L or D configuration, and may be selected from the group consisting of lysine, ornithine, 2,4-diaminobutyric acid, arginine, and homoarginine, preferably L-lysine or D-lysine.

When the polypeptide of the present invention is larger than a nonadecapeptide, the amino acid in position 19 is L-asparagine.

Position 20

When the polypeptide consists of 20 amino acids, the amino acid in position 20 is the C-terminal portion, —NH—*CH(CH$_2$R$_4$)—R$_5$, of the polypeptide, may have the L or D configuration, and may be selected from the group consisting of lysine, ornithine, 2,4-diaminobutyric acid, arginine, and homoarginine, and preferably is L-lysine or D-lysine.

When the polypeptide of the present invention is larger than 20 amino acids, the amino acid in position 20 of the polypeptide is L-lysine.

Position 21

When the polypeptide consists of 21 amino acids, the amino acid in position 21 is the C-terminal portion, —NH—*CH(CH$_2$R$_4$)—R$_5$, of the polypeptide, may have the L or D configuration, and may be selected from the group consisting of lysine, ornithine, 2,4-diaminobutyric acid, arginine, and homoarginine, preferably L-lysine or D-lysine.

When the polypeptide of the present invention is larger than 21 amino acids, the amino acid in position 21 is glycine.

Position 22

The amino acid in position 22 of certain of the polypeptides of this invention is the C-terminal portion, —NH—*CH(CH$_2$R$_4$)—R$_5$, of the polypeptide, may have the L or D configuration, and may be selected from the group consisting of glutamine, lysine, ornithine, 2,4-diaminobutyric acid, arginine, and homoarginine, and preferably is selected from the group consisting of L-lysine, D-lysine, L-glutamine, and D-glutamine.

The C-Terminal Amino Acid, —NH—*CH(CH$_2$R$_4$)R$_5$

The residue present in the C-terminal position, —NH—*CH(CH$_2$R$_4$)—R$_5$, of the polypeptides of this invention is an amino acid with a C-terminal carboxylic acid derivative R$_5$, wherein R$_5$ is —COOH or —CONH$_2$, preferably —CONH$_2$. R$_4$ is as defined above.

The term "cycloalkyl", as used herein, means cyclic hydrocarbon radicals containing from 5 to 7 carbon atoms. Examples of suitable cyclic hydrocarbon radicals are cyclopentyl, cyclohexyl, and cycloheptyl. The term "halogen", as used herein, includes all four halogens with chlorine being preferred.

In a preferred embodiment, the compounds of the present invention are selected from the group consisting of:

H-Phe-Val-Phe-Ile-Phe-Thr-Tyr-Gly-Glu-Leu-Gln-Arg-Leu-Gln-Flu-Arg-Asn-Lys-Gly-Gln-OH (SEQ ID NO:9);

H-Phe-Val-Phe-Ile-Phe-Thr-Tyr-Gly-Glu-Leu-Gln-Arg-Leu-Gln-Glu-Lys-Glu-Arg-Asn-Lys-Gly-Gln-NH$_2$ (SEQ ID NO:10);

H-Phe-Val-D-Phe-Ile-Phe-Thr-Tyr-Gly-Glu-Leu-Gln-Arg-Leu-Gln-Glu-Lys-Glu-Arg-Asn-Lys-Gly-Gln-OH (SEQ ID NO:11);

H-Phe-Val-D-Phe-Ile-Phe-Thr-Tyr-Gly-Glu-Leu-Gln-Arg-Leu-Gln-Glu-Lys-Glu-Arg-Asn-Lys-Gly-Gln-NH$_2$ (SEQ ID NO:12);

H-Phe-Val-Phe-Ile-Phe-Thr-Tyr-Gly-Glu-Leu-Gln-Arg-NH$_2$ (SEQ ID NO:13);

H-Phe-Val-Phe-Ile-Phe-Thr-Tyr-Gly-Glu-Leu-Gln-Arg-Leu-Gln-OH (SEQ ID NO:14);

(N-Me)-Phe-Val-Phe-Ile-Phe-Thr-Tyr-Gly-Glu-Leu-Gln-Arg-Leu-Gln-OH (SEQ ID NO:15);

(Me$_2$N)-Phe-Val-Phe-Ile-Phe-Thr-Tyr-Gly-Glu-Leu-Gln-Arg-Leu-Gln-OH (SEQ ID NO:16);

H-Phe-Val-p-L-Phe-Ile-Phe-Thr-Tyr-Gly-Glu-Leu-Gln-Arg-Leu-Gln-OH (SEQ ID NO:17);

H-Phe-Val-Leu-Ile-Phe-Thr-Tyr-Gly-Glu-Leu-Gln-Arg-Leu-Gln-OH (SEQ ID NO:18);

H-Phe-Val-Thi-Ile-Phe-Thr-Tyr-Gly-Glu-Leu-Gln-Arg-Leu-Gln-OH (SEQ ID NO:19);

H-Phe-Val-Cha-Ile-Phe-Thr-Tyr-Gly-Glu-Leu-Gln-Arg-Leu-Gln-OH (SEQ ID NO:20);

H-Phe-Val-2-Nal-Ile-Phe-Thr-Tyr-Gly-Glu-Leu-Gln-Arg-Leu-Gln-OH (SEQ ID NO:21);

H-Phe-Val-D-Phe-Ile-Phe-Thr-Tyr-Gly-Glu-Leu-Gln-Arg-Leu-Gln-OH (SEQ ID NO:22);

H-Phe-Val-Phe-Leu-Phe-Thr-Tyr-Gly-Glu-Leu-Gln-Arg-Leu-Gln-OH (SEQ ID NO:23):

H-Phe-Val-Phe-Ile-Cha-Thr-Tyr-Gly-Glu-Leu-Gln-Arg-Leu-Gln-OH (SEQ ID NO:24);

H-Phe-Val-Phe-Ile-Ala-Thr-Tyr-Gly-Glu-Leu-Gln-Arg-Leu-Gln-OH (SEQ ID NO:25);

H-Phe-Val-Phe-Ile-Phe-Thr-Phe-Gly-Glu-Leu-Gln-Arg-Leu-Gln-OH (SEQ ID NO:26);

H-Phe-Val-Phe-Ile-Phe-Thr-Tyr-D-Ala-Glu-Leu-Gln-Arg-Leu-Gln-OH (SEQ ID NO:27);

H-Phe-Val-Phe-Ile-Phe-Thr-Tyr-Gly-Gln-Leu-Gln-Arg-Leu-Gln-OH (SEQ ID NO:28):

H-Phe-Val-Phe-Ile-Phe-Thr-Tyr-Gly-Glu-Leu-Ala-Arg-Leu-Gln-OH (SEQ ID NO:29);

H-Phe-Leu-Phe-Ile-Phe-Thr-Tyr-Gly-Glu-Leu-Gln-Arg-Leu-Gln-OH (SEQ ID NO:30);

H-Phe-Val-Phe-Ile-Phe-Thr-Tyr-Gly-Glu-Leu-Gln-Arg-Leu-Gln-NH$_2$ (SEQ ID NO:31);

(N-ME)-Phe-Val-Phe-Ile-Phe-Thr-Tyr-Gly-Glu-Leu-Gln-Arg-Leu-Gln-NH$_2$ (SEQ ID NO:32);

(Me$_2$N)-Phe-Val-Phe-Ile-Phe-Thr-Tyr-Gly-Glu-Leu-Gln-Arg-Leu-Gln-NH$_2$(SEQ ID NO:33);

H-Phe-Val-p-l-Phe-Ile-Phe-Thr-Tyr-Gly-Glu-Leu-Gln-Arg-Leu-Gln-NH$_2$ (SEQ ID NO:34);

H-Phe-Val-Leu-Ile-Phe-Thr-Tyr-Gly-Glu-Leu-Gln-Arg-Leu-Gln-NH$_2$ (SEQ ID NO:35);

H-Phe-Val-Thi-Ile-Phe-Thr-Tyr-Gly-Glu-Leu-Gln-Arg-Leu-Gln-NH$_2$ (SEQ ID NO:36);

H-Phe-Val-Cha-Ile-Phe-Thr-Tyr-Gly-Glu-Leu-Gln-Arg-Leu-Gln-NH$_2$ (SEQ ID NO:37);

H-Phe-Val-2-Nal-Ile-Phe-Thr-Tyr-Gly-Glu-Leu-Gln-Arg-Leu-Gln-NH$_2$ (SEQ ID NO:38);

H-Phe-Val-D-Phe-Ile-Phe-Thr-Tyr-Gly-Glu-Leu-Gln-Arg-Leu-Gln-NH$_2$ (SEQ ID NO:39):

H-Phe-Val-Phe-Leu-Phe-Thr-Tyr-Gly-Glu-Leu-Gln-Arg-Leu-Gln-NH$_2$ (SEQ ID NO:40);

H-Phe-Val-Phe-Ile-Cha-Thr-Tyr-Gly-Glu-Leu-Gln-Arg-Leu-Gln-NH$_2$ (SEQ ID NO:41);

H-Phe-Val-Phe-Ile-Ala-Thr-Tyr-Gly-Glu-Leu-Gln-Arg-Leu-Gln-NH$_2$ (SEQ ID NO:42);

H-Phe-Val-Phe-Ile-Phe-Thr-Phe-Gly-Glu-Leu-Gln-Arg-Leu-Gln-NH$_2$ (SEQ ID NO:43);

H-Phe-Val-Phe-Ile-Phe-Thr-Tyr-D-Ala-Glu-Leu-Gln-Arg-Leu-Gln-NH$_2$ (SEQ ID NO:44);

H-Phe-Val-Phe-Ile-Phe-Thr-Tyr-Gly-Gln-Leu-Gln-Arg-Leu-Gln-NH$_2$ (SEQ ID NO:45);

H-Phe-Val-Phe-Ile-Phe-Thr-Tyr-Gly-Glu-Leu-Ala-Arg-Leu-Gln-NH$_2$ (SEQ ID NO:46);

H-Phe-Leu-Phe-Ile-Phe-Thr-Tyr-Gly-Glu-Leu-Gln-Arg-Leu-Gln-NH$_2$ (SEQ ID NO:47);

H-Phe-Val-Phe-Ile-Phe-Thr-Tyr-Gly-Glu-Leu-Gln-Arg-Leu-Lys-NH$_2$ (SEQ ID NO:48);

H-D-Phe-Val-Phe-Ile-Phe-Thr-Tyr-Gly-Glu-Leu-Gln-Arg-Leu-Gln-OH (SEQ ID NO:49);

H-Cha-Val-Phe-Ile-Phe-Thr-Tyr-Gly-Glu-Leu-Gln-Arg-Leu-Gln-OH (SEQ ID NO:50);

H-Phe-Val-Pal-Ile-Phe-Thr-Tyr-Gly-Glu-Leu-Gln-Arg-Leu-Gln-OH (SEQ ID NO:51);

H-D-Phe-Val-Phe-Ile-Phe-Thr-Tyr-Gly-Glu-Leu-Gln-Arg-Leu-Gln-NH$_2$ (SEQ ID NO:52);

H-Cha-Val-Phe-Ile-Phe-Thr-Tyr-Gly-Glu-Leu-Gln-Arg-Leu-Gln-NH$_2$ (SEQ ID NO:53);

H-Phe-Val-Pal-Ile-Phe-Thr-Tyr-Gly-Glu-Leu-Gln-Arg-Leu-Gln-NH$_2$ (SEQ ID NO:54);

H-Phe-Val-Phe-Ile-Phe-Thr-Tyr-Gly-Glu-Leu-Gln-Arg-Leu-D-Gln-NH$_2$ (SEQ ID NO:55);

H-Phe-Val-D-Phe-Ile-Phe-Thr-Tyr-Gly-Glu-Leu-Gln-Arg-NH$_2$ (SEQ ID NO:56);

H-Phe-Val-D-Phe-Ile-Phe-Thr-Tyr-Gly-Glu-Leu-Gln-Arg-Leu-Gln-OH (SEQ ID NO:57);

(N-Me)-Phe-Val-D-Phe-Ile-Phe-Thr-Tyr-Gly-Glu-Leu-Gln-Arg-Leu-Gln-OH (SEQ ID NO:58);

(Me$_2$N)-Phe-Val-D-Phe-Ile-Phe-Thr-Tyr-Gly-Glu-Leu-Gln-Arg-Leu-Gln-OH (SEQ ID NO:59);

H-Phe-Val-D-Phe-Leu-Phe-Thr-Tyr-Gly-Glu-Leu-Gln-Arg-Leu-Gln-OH (SEQ ID NO:60);

H-Phe-Val-D-Phe-Ile-Cha-Thr-Tyr-Gly-Glu-Leu-Gln-Arg-Leu-Gln-OH (SEQ ID NO:61);

H-Phe-Val-D-Phe-Ile-Ala-Thr-Tyr-Gly-Glu-Leu-Gln-Arg-Leu-Gln-OH (SEQ ID NO:62);

H-Phe-Val-D-Phe-Ile-Phe-Thr-Phe-Gly-Glu-Leu-Gln-Arg-Leu-Gln-OH (SEQ ID NO:63);

H-Phe-Val-D-Phe-Ile-Phe-Thr-Tyr-D-Ala-Glu-Leu-Gln-Arg-Leu-Gln-OH (SEQ ID NO:64);

H-Phe-Val-D-Phe-ILe-Phe-Thr-Tyr-Gly-Gln-Leu-Gln-Arg-Leu-Gln-OH (SEQ ID NO:65);

H-Phe-Val-D-Phe-Ile-Phe-Thr-Tyr-Gly-Glu-Leu-Ala-Arg-Leu-Gln-OH (SEQ ID NO:66);

H-Phe-Leu-D-Phe-Ile-Phe-Thr-Tyr-Gly-Glu-Leu-Gln-Arg-Leu-Gln-Oh (SEQ ID NO:67);
H-Phe-Val-D-Phe-Ile-Phe-Thr-Tyr-Gly-Glu-Leu-Gln-Arg-Leu-Gln-NH$_2$ (SEQ ID NO:68);
(N-Me)-Phe-Val-D-Phe-Ile-Phe-Thr-Tyr-Gly-Glu-Leu-Gln-Arg-Leu-Gln-NH$_2$ (SEQ ID NO:69);
(Me$_2$N)-Phe-Val-D-Phe-Ile-Phe-Thr-Tyr-Gly-Glu-Leu-Gln-Arg-Leu-Gln-NH$_2$ (SEQ ID NO:70);
H-Phe-Val-D-Phe-Leu-Phe-Thr-Tyr-Gly-Glu-Leu-Gln-Arg-Leu-Gln-NH$_2$ (SEQ ID NO:71);
H-Phe-Val-D-Phe-Lle-Cha-Thr-Tyr-Gly-Glu-Leu-Gln-Arg-Leu-Gln-NH$_2$ (SEQ ID NO:72);
H-Phe-Val-D-Phe-Ile-Ala-Thr-Tyr-Gly-Glu-Leu-Gln-Arg-Leu-Gln-NH$_2$ (SEQ ID NO:73);
H-Phe-Val-D-Phe-Ile-Phe-Thr-Phe-Gly-Glu-Leu-Gln-Arg-Leu-Gln-NH$_2$ (SEQ ID NO:74);
H-Phe-Val-D-Phe-ILe-Phe-Thr-Tyr-D-Ala-Glu-Leu-Gln-Arg-Leu-Gln-NH$_2$ (SEQ ID NO:75);
H-Phe-Val-D-Phe-Ile-Phe-Thr-Tyr-Gly-Gln-Leu-Gln-Arg-Leu-Gln-NH$_2$ (SEQ ID NO:76);
H-Phe-Val-D-Phe-Ile-Phe-Thr-Tyr-Gly-Glu-Leu-Ala-Arg-Leu-Gln-NH$_2$ (SEQ ID NO:77);
H-Phe-Leu-D-Phe-Ile-Phe-Thr-Tyr-Gly-Glu-Leu-Gln-Arg-Leu-Gln-NH$_2$ (SEQ ID NO:78);
H-Phe-Val-D-Phe-Ile-Phe-Thr-Tyr-Gly-Glu-Leu-Gln-Arg-Leu-Lys-NH$_2$ (SEQ ID NO:79);
H-D-Phe-Val-D-Phe-Ile-Phe-Thr-Tyr-Gly-Glu-Leu-Gln-Arg-Leu-Gln-OH (SEQ ID NO:80);
H-Cha-Val-D-Phe-Ile-Phe-Thr-Tyr-Gly-Glu-Leu-Gln-Arg-Leu-Gln-OH (SEQ ID NO:81);
H-Phe-Val-Pal-Ile-Phe-Thr-Tyr-Gly-Glu-Leu-Gln-Arg-Leu-Gln-OH (SEQ ID NO:82);
H-D-Phe-Val-D-Phe-Ile-Phe-Thr-Tyr-Gly-Glu-Leu-Gln-Arg-Leu-Gln-NH$_2$ (SEQ ID NO:83);
H-Cha-Val-D-Phe-Ile-Phe-Thr-Tyr-Gly-Glu-Leu-Gln-Arg-Leu-Gln-NH$_2$ (SEQ ID NO:84);
H-Phe-Val-Pal-Ile-Phe-Thr-Tyr-Gly-Glu-Leu-Gln-Arg-Leu-Gln-NH$_2$ (SEQ ID NO:85);
H-Phe-Val-D-Phe-Ile-Phe-Thr-Tyr-Gly-Glu-Leu-Gln-Arg-Leu-D-Gln-NH$_2$ (SEQ ID NO:86);
(N-Me)-Phe-Val-D-Phe-Ile-Phe-Thr-Tyr-Gly-Glu-Leu-Gln-Arg-Leu-D-Gln-NH$_2$ (SEQ ID NO:87);
(Me$_2$N)-Phe-Val-D-Phe-Ile-Phe-Thr-Tyr-Gly-Glu-Leu-Gln-Arg-Leu-D-Gln-NH$_2$ (SEQ ID NO:88);
(N-Me)-Phe-Val-Phe-Ile-Phe-Thr-Tyr-Gly-Glu-Leu-Gln-Arg-Leu-D-Gln-NH$_2$ (SEQ ID NO:89);
(Me$_2$N)-Phe-Val-Phe-Ile-Phe-Thr-Tyr-Gly-Glu-Leu-Gln-Arg-Leu-D-Gln-NH$_2$ (SEQ ID NO:90);
(N-Me)-Phe-Val-D-Phe-Ile-Phe-Thr-Tyr-Gly-Glu-Leu-Gln-D-Arg-Leu-Gln-NH$_2$ (SEQ ID NO:91);
(Me$_2$N)-Phe-Val-D-Phe-Ile-Phe-Thr-Tyr-Gly-Glu-Leu-Gln-D-Arg-Leu-Gln-NH$_2$ (SEQ ID NO:92):
(N-Me)-Phe-Val-Phe-Ile-Phe-Thr-Tyr-Gly-Glu-Leu-Gln-D-Arg-Leu-Gln-NH$_2$ (SEQ ID NO:93);
(Me$_2$N)-Phe-Val-Phe-Ile-Phe-Thr-Tyr-Gly-Glu-Leu-Gln-D-Arg-Leu-Gln-NH$_2$ (SEQ ID NO:94);
(N-Me)-Phe-Val-D-Phe-Ile-Phe-Thr-Tyr-Gly-Glu-Leu-Gln-Arg-Leu-Lys—NH$_2$ (SEQ ID NO:95):
(Me$_2$N)-Phe-Val-D-Phe-Ile-Phe-Thr-Tyr-Gly-Glu-Leu-Gln-Arg-Leu-Lys-NH$_2$ (SEQ ID NO:96);
(N-Me)-Phe-Val-Phe-Ile-Phe-Thr-Tyr-Gly-Glu-Leu-Gln-Arg-Leu-Lys-NH$_2$ (SEQ ID NO:97);
(Me$_2$N)-Phe-Val-Phe-Ile-Phe-Thr-Tyr-Gly-Glu-Leu-Gln-Arg-Leu-Lys-NH$_2$ (SEQ ID NO:98);
(N-Me)-Phe-Val-D-Phe-Ile-Phe-Thr-Tyr-Gly-Glu-Leu-Gln-D-Arg-Leu-Lys-NH$_2$ (SEQ ID NO:99);
(Me$_2$N)-Phe-Val-D-Phe-Ile-Phe-Thr-Tyr-Gly-Glu-Leu-Gln-D-Arg-Leu-Lys-NH$_2$ (SEQ ID NO:100);
(N-Me)-Phe-Val-Phe-Ile-Phe-Thr-Tyr-Gly-Glu-Leu-Gln-D-Arg-Leu-Lys-NH$_2$ (SEQ ID NO:101);
(Me$_2$N)-Phe-Val-Phe-Ile-Phe-Thr-Tyr-Gly-Glu-Leu-Gln-D-Arg-Leu-Lys-NH$_2$ (SEQ ID NO:102);
(N-Me)-Phe-Val-D-Phe-Ile-Phe-Thr-Tyr-Gly-Glu-Leu-Gln-Arg-Leu-D-Lys-NH$_2$ (SEQ ID NO:103);
(Me$_2$N)=Phe-Val-D-Phe-Ile-Phe-Thr-Tyr-Gly-Glu-Leu-Gln-Arg-Leu-D-Lys-NH$_2$ (SEQ ID NO:104):
(N-ME)-Phe-Val-Phe-Ile-Phe-Thr-Tyr-Gly-Glu-Leu-Gln-Arg-Leu-D-Lys-NH$_2$ (SEQ ID NO:105);
(Me$_2$N)-Phe-Val-Phe-Ile-Phe-Thr-Tyr-Gly-Glu-Leu-Gln-Arg-Leu-D-Lys-NH$_2$ (SEQ ID NO:106);
(N-Me)-Phe-Val-D-Phe-Ile-Phe-Thr-Tyr-Gly-Glu-Leu-Gln-D-Arg-Leu-D-Lys-NH$_2$ (SEQ ID NO:107);
(Me$_2$N)-Phe-Val-D-Phe-Ile-Phe-Thr-Tyr-Gly-Glu-Leu-Gln-D-Arg-Leu-D-Lys-NH$_2$ (SEQ ID NO:108);
(N-Me)-Phe-Val-Phe-Ile-Phe-Thr-Tyr-Gly-Glu-Leu-Gln-D-Arg-Leu-D-Lys-NH$_2$ (SEQ ID NO:109);
(Me$_2$N)-Phe-Val-Phe-Ile-Phe-Thr-Tyr-Gly-Glu-Leu-Gln-D-Arg-Leu-D-Lys-NH$_2$ (SEQ ID NO:110):
(N-Me)-Phe-Val-D-Phe-Ile-Phe-Thr-Tyr-Gly-Glu-Leu-Gln-D-Arg-Leu-D-Gln-NH$_2$ (SEQ ID NO:111);
(Me$_2$N)-Phe-Val-D-Phe-Ile-Phe-Thr-Tyr-Gly-Glu-Leu-Gln-D-Arg-Leu-D-Gln-NH$_2$ (SEQ ID NO:112);
(N-Me)-Phe-Val-Phe-Ile-Phe-Thr-Tyr-Gly-Glu-Leu-Gln-D-Arg-Leu-D-Gln-NH$_2$ (SEQ ID NO:113);
(Me$_2$N)-Phe-Val-Phe-Ile-Phe-Thr-Tyr-Gly-Glu-Leu-Gln-D-Arg-Leu-D-Gln-NH$_2$ (SEQ ID NO:114);
(N-Me)-Phe-Val-D-Phe-Ile-Phe-Thr-Tyr-Gly-Glu-Leu-Ala-Arg-Leu-Gln-NH$_2$ (SEQ ID NO:115);
(Me$_2$N)-Phe-Val-D-Phe-Ile-Phe-Thr-Tyr-Gly-Glu-Leu-Ala-Arg-Leu-Gln-NH$_2$ (SEQ ID NO:116);
(N-Me)-Phe-Val-Phe-Ile-Phe-Thr-Tyr-Gly-Glu-Leu-Ala-Arg-Leu-Gln-NH$_2$ (SEQ ID NO:117);
(Me$_2$N)-Phe-Val-Phe-Ile-Phe-Thr-Tyr-Gly-Glu-Leu-Ala-Arg-Leu-Gln-NH$_2$ (SEQ ID NO:118);
(N-Me)-Phe-Val-D-Phe-Ile-Phe-Thr-Tyr-Gly-Glu-Leu-Ala-Arg-Leu-D-Gln-NH$_2$ (SEQ ID NO:119);
(Me$_2$N)-Phe-Val-D-Phe-ILe-Phe-Thr-Tyr-Gly-Glu-Leu-Ala-Arg-Leu-D-Gln-NH$_2$ (SEQ ID NO:120);
(N-Me)-Phe-Val-Phe-Ile-Phe-Thr-Tyr-Gly-Glu-Leu-Ala-Arg-Leu-D-Gln-NH$_2$ (SEQ ID NO:121);
(Me$_2$N)-Phe-Val-Phe-Ile-Phe-Thr-Tyr-Gly-Glu-Leu-Ala-Arg-Leu-D-Gln-NH$_2$ (SEQ ID NO:122);
(N-Me)-Phe-Val-D-Phe-Ile-Phe-Thr-Tyr-Gly-Glu-Leu-Ala-D-Arg-Leu-Gln-NH$_2$ (SEQ ID NO:123);
(Me$_2$N)-Phe-Val-D-Phe-Ile-Phe-Thr-Tyr-Gly-Glu-Leu-Ala-D-Arg-Leu-Gln-NH$_2$ (SEQ ID NO:124);
(N-Me)-Phe-Val-Phe-Ile-Phe-Thr-Tyr-Gly-Glu-Leu-Ala-D-Arg-Leu-Gln-NH$_2$ (SEQ ID NO:125);
(Me$_2$N)-Phe-Val-Phe-Ile-Phe-Thr-Tyr-Gly-Glu-Leu-Ala-D-Arg-Leu-Gln-NH$_2$ (SEQ ID NO:126);
(N-Me)-Phe-Val-D-Phe-Ile-Phe-Thr-Tyr-Gly-Glu-Leu-Ala-D-Arg-Leu-D-Gln-NH$_2$ (SEQ ID NO:127);
(Me$_2$N)-Phe-Val-D-Phe-Ile-Phe-Thr-Tyr-Gly-Glu-Leu-Ala-D-Arg-Leu-D-Gln-NH$_2$ (SEQ ID NO:128);
(N-Me)-Phe-Val-Phe-Ile-Phe-Thr-Tyr-Gly-Glu-Leu-Ala-D-Arg-Leu-D-Gln-NH$_2$ (SEQ ID NO:129);
(Me$_2$N)-Phe-Val-Phe-Ile-Phe-Thr-Tyr-Gly-Glu-Leu-Ala-D-Arg-Leu-D-Gln-NH$_2$ (SEQ ID NO:130);
(N-Me)-Phe-Val-D-Phe-Ile-Phe-Thr-Tyr-Gly-Glu-Leu-Ala-D-Arg-Leu-Lys-NH$_2$ (SEQ ID NO:131);
(Me$_2$N)-Phe-Val-D-Phe-Ile-Phe-Thr-Tyr-Gly-Glu-Leu-Ala-D-Arg-Leu-Lys-NH$_2$ (SEQ ID NO:132);
(N-Me)-Phe-Val-Phe-Ile-Phe-Thr-Tyr-Gly-Glu-Leu-Ala-D-Arg-Leu-Lys-NH$_2$ (SEQ ID NO:133);
(Me$_2$N)-Phe-Val-Phe-Ile-Phe-Thr-Tyr-Gly-Glu-Leu-Ala-D-Arg-Leu-Lys-NH$_2$ (SEQ ID NO:134);

(N-Me)-Phe-Val-D-Phe-Ile-Phe-Thr-Tyr-Gly-Glu-Leu-Ala-D-Arg-Leu-D-Lys-NH$_2$ (SEQ ID NO:135);
(Me$_2$N)-Phe-Val-D-Phe-Ile-Phe-Thr-Tyr-Gly-Glu-Leu-Ala-D-Arg-Leu-D-Lys-NH$_2$ (SEQ ID NO:136);
(N-Me)-Phe-Val-Phe-Ile-Phe-Thr-Tyr-Gly-Glu-Leu-Ala-D-Arg-Leu-D-Lys-NH$_2$ (SEQ ID NO:137);
(Me$_2$N)-Phe-Val-Phe-Ile-Phe-Thr-Tyr-Gly-Glu-Leu-Ala-D-Arg-Leu-D-Lys-NH$_2$ (SEQ ID NO:138);
(N-Me)-Phe-Val-D-Phe-Ile-Phe-Thr-Tyr-Gly-Glu-Leu-Gln-Arg-NH$_2$ (SEQ ID NO:139);
(Me$_2$N)-Phe-Ile-Phe-Thr-Tyr-Gly-Glu-Leu-Gln-Arg-NH$_2$ (SEQ ID NO:140);
(N-Me)-Phe-Val-Phe-Ile-Phe-Thr-Tyr-Gly-Glu-Leu-Gln-Arg-NH$_2$ (SEQ ID NO:141);
(Me$_2$N)-Phe-Val-Phe-Ile-Phe-Thr-Tyr-Gly-Glu-Leu-Gln-Arg-NH$_2$ (SEQ ID NO:142);
(N-Me)-Phe-Val-D-Phe-Ile-Phe-Thr-Tyr-Gly-Glu-Leu-Ala-Arg-NH$_2$ (SEQ ID NO:143);
(Me$_2$N)-Phe-Val-D-Phe-Ile-Phe-Thr-Tyr-Gly-Glu-Leu-Ala-Arg-NH$_2$ (SEQ ID NO:144);
(N-Me)-Phe-Val-Phe-Ile-Phe-Thr-Tyr-Gly-Glu-Leu-Ala-Arg-NH$_2$ (SEQ ID NO:145);
(Me$_2$N)-Phe-Val-Phe-Ile-Phe-Thr-Tyr-Gly-Glu-Leu-Ala-Arg-NH$_2$ (SEQ ID NO: 146);
(N-Me)-Phe-Val-D-Phe-Ile-Phe-Thr-Tyr-Gly-Glu-Leu-Gln-D-Arg—NH$_2$ (SEQ ID NO:147);
(Me$_2$N)-Phe-Val-D-Phe-Ile-Phe-Thr-Tyr-Gly-Glu-Leu-Gln-D-Arg-NH$_2$ (SEQ ID NO:148):
(N-Me)-Phe-Val-Phe-Ile-Phe-Thr-Tyr-Gly-Glu-Leu-Gln-D-Arg-NH$_2$ (SEQ ID NO:149);
(Me$_2$N)-Phe-Val-Phe-Ile-Phe-Thr-Tyr-Gly-Glu-Leu-Gln-D-Arg-NH$_2$ (SEQ ID NO:150):
(N-Me)-Phe-Val-D-Phe-Ile-Phe-Thr-Tyr-Gly-Glu-Leu-Ala-D-Arg-NH$_2$ (SEQ ID NO:151):
(Me$_2$N)-Phe-Val-D-Phe-Ile-Phe-Thr-Tyr-Gly-Glu-Leu-Ala-D-Arg-NH$_2$ (SEQ ID NO:152):
(N-Me)-Phe-Val-Phe-Ile-Phe-Thr-Tyr-Gly-Glu-Leu-Ala-D-Arg-NH$_2$ (SEQ ID NO:153); and
(Me$_2$N)-Phe-Val-Phe-Ile-Phe-Thr-Tyr-Gly-Glu-Leu-Ala-D-Arg-NH$_2$ (SEQ ID NO:154);
and their pharmaceutically acceptable addition salts. In each case, the amino acids have the L-configuration unless otherwise specified. In a more preferred embodiment, the compounds of the present invention are selected from the group consisting of
H-Phe-Val-Phe-Ile-Phe-Thr-Tyr-Gly-Glu-Leu-Gln-Arg-Leu-Glu-Lys-Glu-Arg-Asn-Lys-Gly-Gln-OH (SEQ ID NO:9);
H-Phe-Val-Phe-Ile-Phe-Thr-Tyr-Gly-Glu-Leu-Gln-Arg-Leu-Glu-Lys-glu-Arg-Asn-Lys-Gly-Gln-NH$_2$ (SEQ ID NO:10);
H-Phe-Val-D-Phe-Ile-Phe-Thr-Tyr-Gly-Glu-Leu-Gln-Arg-Leu-Glu-Lys-Glu-Arg-Asn-Lys-Gly-Gln-OH (SEQ ID NO:11);
H-Phe-Val-D-Phe-Ile-Phe-Thr-Tyr-Gly-Glu-Leu-Gln-Arg-Leu-Glu-Lys-Glu-Arg-Asn-Lys-Gly-gln-NH$_2$ (SEQ ID NO:12);
H-Phe-Val-Phe-Ile-Phe-Thr-Tyr-Gly-Glu-Leu-Gln-Arg-NH$_2$ (SEQ ID NO:13);
H-Phe-Val-Phe-Ile-Phe-Thr-Tyr-Gly-Glu-Leu-Gln-Arg-Leu-Gln-OH (SEQ ID NO:14);
(N-Me)-Phe-Val-Phe-Ile-Phe-Thr-Tyr-Gly-Glu-Leu-Gln-Arg-Leu-Gln-OH (SEQ ID NO:15);
(Me$_2$N)-Phe-Val-Phe-Ile-Phe-Thr-Tyr-Gly-Glu-Leu-Gln-Arg-Leu-Gln-OH (SEQ ID NO:16;);
H-Phe-Val-D-Phe-Ile-Phe-Thr-Tyr-Gly-Glu-Leu-Gln-Arg-Leu-Gln-OH (SEQ ID NO:22);
H-Phe-Val-Phe-Ile-Phe-Thr-Tyr-Gly-Glu-Leu-Gln-Arg-Leu-Gln-NH$_2$ (SEQ ID NO:31);
(N-Me)-Phe-Val-Phe-Ile-Phe-Thr-Tyr-Gly-Glu-Leu-Gln-Arg-Leu-Gln-NH$_2$ (SEQ ID NO:32);
(Me$_2$N)-Phe-Val-Phe-Ile-Phe-Thr-Tyr-Gly-Glu-Leu-Gln-Arg-Leu-Gln-NH$_2$ (SEQ ID NO:33);
H-Phe-Val-Phe-Ile-Phe-Thr-Tyr-Gly-Glu-Leu-Gln-Arg-Leu-Lys-NH$_2$ (SEQ ID NO:48);
H-Phe-Val-Phe-Ile-Phe-Thr-Tyr-Gly-Glu-Leu-Gln-Arg-Leu-D-Gln-NH$_2$ (SEQ ID NO:55);
H-Phe-Val-D-Phe-Ile-Phe-Thr-Tyr-Gly-Glu-Leu-Gln-Arg-NH$_2$ (SEQ ID NO:56);
H-Phe-Val-D-Phe-Ile-Phe-Thr-Tyr-Gly-Glu-Leu-Gln-Arg-Leu-Gln-OH (SEQ ID NO:57);
(N-Me)-Phe-Val-D-Phe-Ile-Phe-Thr-Tyr-Gly-Glu-Leu-Gln-Arg-Leu-Gln-OH (SEQ ID NO:58);
(Me$_2$N)-Phe-Val-D-Phe-Ile-Phe-Thr-Tyr-Gly-Glu-Leu-Gln-Arg-Leu-Gln-OH (SEQ ID NO:59);
H-Phe-Val-D-Phe-Ile-Phe-Thr-Tyr-Gly-Glu-Leu-Gln-Arg-Leu-Gln-NH$_2$ (SEQ ID NO:68);
(N-Me)-Phe-Val-D-Phe-Ile-Phe-Thr-Tyr-Gly-Glu-Leu-Gln-Arg-Leu-Gln-NH$_2$ (SEQ ID NO:69);
(Me$_2$N)-Phe-Val-D-Phe-Ile-Phe-Thr-Tyr-Gly-Glu-Leu-Gln-Arg-Leu-Gln-NH$_2$ (SEQ ID NO:70);
H-Phe-Val-D-Phe-Ile-Phe-Thr-Tyr-Gly-Glu-Leu-Gln-Arg-Leu-Lys-NH$_2$ (SEQ ID NO:79);
H-Phe-Val-D-Phe-Ile-Phe-Thr-Tyr-Gly-Glu-Leu-Gln-Arg-Leu-D-Gln-NH$_2$ (SEQ ID NO:86);
(N-Me)-Phe-Val-D-Phe-Ile-Phe-Thr-Tyr-Gly-Glu-Leu-Gln-Arg-Leu-D-Gln-NH$_2$ (SEQ ID NO:87);
(Me$_2$N)-Phe-Val-D-Phe-Ile-Phe-Thr-Tyr-Gly-Glu-Leu-Gln-Arg-Leu-D-Gln-NH$_2$ (SEQ ID NO:88);
(N-Me)-Phe-Val-Phe-Ile-Phe-Thr-Tyr-Gly-Glu-Leu-Gln-Arg-Leu-D-Gln-NH$_2$ (SEQ ID NO:89);
(Me$_2$N)-Phe-Val-Phe-Ile-Phe-Thr-Tyr-Gly-Glu-Leu-Gln-Arg-Leu-D-Gln-NH$_2$ (SEQ ID NO:90);
(N-Me)-Phe-Val-D-Phe-Ile-Phe-Thr-Tyr-Gly-Glu-Leu-Gln-D-Arg-Leu-Gln-NH$_2$ (SEQ ID NO:91);
(Me$_2$N)-Phe-Val-D-Phe-Ile-Phe-Thr-Tyr-Gly-Glu-Leu-Gln-D-Arg-Leu-Gln-NH$_2$ (SEQ ID NO:92);
(N-Me)-Phe-Val-Phe-Ile-Phe-Thr-Tyr-Gly-Glu-Leu-Gln-D-Arg-Leu-Gln-NH$_2$ (SEQ ID NO:93);
(Me$_2$N)-Phe-Val-Phe-Ile-Phe-Thr-Tyr-Gly-Glu-Leu-Gln-D-Arg-Leu-Gln-NH$_2$ (SEQ ID NO:94);
(N-Me)-Phe-Val-D-Phe-Ile-Phe-Thr-Tyr-Gly-Glu-Leu-Gln-Arg-Leu-Lys-NH$_2$ (SEQ ID NO:95);
(Me$_2$N)-Phe-Val-D-Phe-Ile-Phe-Thr-Tyr-Gly-Glu-Leu-Gln-Arg-Leu-Lys-NH$_2$ (SEQ ID NO:96);
(N-Me)-Phe-Val-Phe-Ile-Phe-Thr-Tyr-Gly-Glu-Leu-Gln-Arg-Leu-Lys-NH$_2$ (SEQ ID NO:97);
(Me$_2$N)-Phe-Val-Phe-Ile-Phe-Thr-Tyr-Gly-Glu-Leu-Gln-Arg-Leu-Lys-NH$_2$ (SEQ ID NO:98);
(N-Me)-Phe-Val-D-Phe-Ile-Phe-Thr-Tyr-Gly-Glu-Leu-Gln-D-Arg-Leu-Lys-NH$_2$(SEQ ID NO:99);
(Me$_2$N)-Phe-Val-D-Phe-Ile-Phe-Thr-Tyr-Gly-Glu-Leu-Gln-D-Arg-Leu-Lys-NH$_2$(SEQ ID NO:100);
(N-Me)-Phe-Val-Phe-Ile-Phe-Thr-Tyr-Gly-Glu-Leu-Gln-D-Arg-Leu-Lys-NH$_2$ (SEQ ID NO:101);
(Me$_2$N)-Phe-Val-Phe-Ile-Phe-Thr-Tyr-Gly-Glu-Leu-Gln-D-Arg-Leu-Lys-NH$_2$ (SEQ ID NO:102);
(N-Me)-Phe-Val-D-Phe-Ile-Phe-Thr-Tyr-Gly-Glu-Leu-Gln-Arg-Leu-D-Lys-NH$_2$ (SEQ ID NO:103);
(Me$_2$N)-Phe-Val-D-Phe-Ile-Phe-Thr-Tyr-Gly-Glu-Leu-Gln-Arg-Leu-D-Lys-NH$_2$(SEQ ID NO:104);
(N-Me)-Phe-Val-Phe-Ile-Phe-Thr-Tyr-Gly-Glu-Leu-Gln-Arg-Leu-D-Lys-NH$_2$ (SEQ ID NO:105);
(Me$_2$N)-Phe-Val-Phe-Ile-Phe-Thr-Tyr-Gly-Glu-Leu-Gln-Arg-Leu-D-Lys-NH$_2$ (SEQ ID NO:106);

(N-Me)-Phe-Val-D-Phe-Ile-Phe-Thr-Tyr-Gly-Glu-Leu-Gln-
D-Arg-Leu-D-Lys-NH$_2$(SEQ ID NO:107);
(Me$_2$N)-Phe-Val-D-Phe-Ile-Phe-Thr-Tyr-Gly-Glu-Leu-Gln-
D-Arg-Leu-D-Lys-NH$_2$(SEQ ID NO:108);
(N-Me)-Phe-Val-Phe-Ile-Phe-Thr-Tyr-Gly-Glu-Leu-Gln-D-
Arg-Leu-D-Lys-NH$_2$ (SEQ ID NO:109);
(Me$_2$N)-Phe-Val-Phe-Ile-Phe-Thr-Tyr-Gly-Glu-Leu-Gln-D-
Arg-Leu-D-Lys-NH$_2$ (SEQ ID NO:110):
(N-Me)-Phe-Val-D-Phe-Ile-Phe-Thr-Tyr-Gly-Glu-Leu-Gln-
D-Arg-Leu-D-Gln-NH$_2$ (SEQ ID NO:111);
(Me$_2$N)-Phe-Val-D-Phe-Ile-Phe-Thr-Tyr-Gly-Glu-Leu-Gln-
D-Arg-Leu-D-Gln-NH$_2$ (SEQ ID NO:112);
(N-Me)-Phe-Val-Phe-Ile-Phe-Thr-Tyr-Gly-Glu-Leu-Gln-D-
Arg-Leu-D-Gln-NH$_2$ (SEQ ID NO:113);
(Me$_2$N)-Phe-Val-Phe-Ile-Phe-Thr-Tyr-Gly-Glu-Leu-Gln-D-
Arg-Leu-D-Gln-NH$_2$ (SEQ ID NO:114);
(N-Me)-Phe-Val-D-Phe-Ile-Phe-Thr-Tyr-Gly-Glu-Leu-Ala-
Arg-Leu-Gln-NH$_2$ (SEQ ID NO:115);
(Me$_2$N)-Phe-Val-D-Phe-Ile-Phe-Thr-Tyr-Gly-Glu-Leu-Ala-
Arg-Leu-Gln-NH$_2$ (SEQ ID NO:116);
(N-Me)-Phe-Val-Phe-Ile-Phe-Thr-Tyr-Gly-Glu-Leu-Ala-
Arg-Leu-Gln-NH$_2$ (SEQ ID NO:117);
(Me$_2$N)-Phe-Val-Phe-Ile-Phe-Thr-Tyr-Gly-Glu-Leu-Ala-
Arg-Leu-Gln-NH$_2$ (SEQ ID NO:118);
(N-Me)-Phe-Val-D-Phe-Ile-Phe-Thr-Tyr-Gly-Glu-Leu-Ala-
Arg-Leu-D-Gln-NH$_2$ (SEQ ID NO:119);
(Me$_2$N)-Phe-Val-D-Phe-Ile-Phe-Thr-Tyr-Gly-Glu-Leu-Ala-
Arg-Leu-D-Gln-NH$_2$ (SEQ ID NO:120);
(N-Me)-Phe-Val-Phe-Ile-Phe-Thr-Tyr-Gly-Glu-Leu-Ala-
Arg-Leu-D-Gln-NH$_2$ (SEQ ID NO:121);
(Me$_2$N)-Phe-Val-Phe-Ile-Phe-Thr-Tyr-Gly-Glu-Leu-Ala-
Arg-Leu-D-Gln-NH$_2$ (SEQ ID NO:122);
(N-Me)-Phe-Val-D-Phe-Ile-Phe-Thr-Tyr-Gly-Glu-Leu-Ala-
D-Arg-Leu-Gln-NH$_2$ (SEQ ID NO:123);
(Me$_2$N)-Phe-Val-D-Phe-Ile-Phe-Thr-Tyr-Gly-Glu-Leu-Ala-
D-Arg-Leu-Gln-NH$_2$ (SEQ ID NO:124);
(N-Me)-Phe-Val-Phe-Ile-Phe-Thr-Tyr-Gly-Glu-Leu-Ala-D-
Arg-Leu-Gln-NH$_2$ (SEQ ID NO:125);
(Me$_2$N)-Phe-Val-Phe-Ile-Phe-Thr-Tyr-Gly-Glu-Leu-Ala-D-
Arg-Leu-Gln-NH$_2$ (SEQ ID NO:126);
(N-Me)-Phe-Val-D-Phe-Ile-Phe-Thr-Tyr-Gly-Glu-Leu-Ala-
D-Arg-Leu-D-Gln-NH$_2$(SEQ ID NO:127);
(Me$_2$N)-Phe-Val-D-Phe-Ile-Phe-Thr-Tyr-Gly-Glu-Leu-Ala-
D-Arg-Leu-D-Gln-NH$_2$ (SEQ ID NO:128);
(N-Me)-Phe-Val-Phe-Ile-Phe-Thr-Tyr-Gly-Glu-Leu-Ala-D-
Arg-Leu-D-Gln-NH$_2$ (SEQ ID NO:129);
(Me$_2$N)-Phe-Val-Phe-Ile-Phe-Thr-Tyr-Gly-Glu-Leu-Ala-D-
Arg-Leu-D-Gln-NH$_2$ (SEQ ID NO:130);
(N-Me)-Phe-Val-D-Phe-Ile-Phe-Thr-Tyr-Gly-Glu-Leu-Ala-
D-Arg-Leu-Lys-NH$_2$ (SEQ ID NO:131);
(Me$_2$N)-Phe-Val-D-Phe-Ile-Phe-Thr-Tyr-Gly-Glu-Leu-Ala-
D-Arg-Leu-Lys-NH$_2$ (SEQ ID NO:132);
(N-Me)-Phe-Val-Phe-Ile-Phe-Thr-Tyr-Gly-Glu-Leu-Ala-D-
Arg-Leu-Lys-NH$_2$ (SEQ ID NO:133);
(Me$_2$N)-Phe-Val-Phe-Ile-Phe-Thr-Tyr-Gly-Glu-Leu-Ala-D-
Arg-Leu-Lys-NH$_2$ (SEQ ID NO:134);
(N-Me)-Phe-Val-D-Phe-Ile-Phe-Thr-Tyr-Gly-Glu-Leu-Ala-
D-Arg-Leu-D-Lys-NH$_2$ (SEQ ID NO:135);
(Me$_2$N)-Phe-Val-D-Phe-Ile-Phe-Thr-Tyr-Gly-Glu-Leu-Ala-
D-Arg-Leu-D-Lys-NH$_2$ (SEQ ID NO:136);
(N-Me)-Phe-Val-Phe-Ile-Phe-Thr-Tyr-Gly-Glu-Leu-Ala-D-
Arg-Leu-D-Lys-NH$_2$ (SEQ ID NO:137);
(Me$_2$N)-Phe-Val-Phe-Ile-Phe-Thr-Tyr-Gly-Glu-Leu-Ala-D-
Arg-Leu-D-Lys-NH$_2$ (SEQ ID NO:138);
(N-Me)-Phe-Val-D-Phe-Ile-Phe-Thr-Tyr-Gly-Glu-Leu-Gln-
Arg-NH$_2$ (SEQ ID NO:139);
(Me$_2$N)-Phe-Val-D-Phe-Ile-Phe-Thr-Tyr-Gly-Glu-Leu-Gln-
Arg-NH$_2$ (SEQ ID NO:140);
(N-Me)-Phe-Val-Phe-Ile-Phe-Thr-Tyr-Gly-Glu-Leu-Gln-
Arg-NH$_2$ (SEQ ID NO:141);
(Me$_2$N)-Phe-Val-Phe-Ile-Phe-Thr-Tyr-Gly-Glu-Leu-Gln-
Arg-NH$_2$ (SEQ ID NO:142);
(N-Me)-Phe-Val-D-Phe-Ile-Phe-Thr-Tyr-Gly-Glu-Leu-Ala-
Arg-NH$_2$ (SEQ ID NO:143);
(Me$_2$N)-Phe-Val-D-Phe-Ile-Phe-Thr-Tyr-Gly-Glu-Leu-Ala-
Arg-NH$_2$ (SEQ ID NO:144);
(N-Me)-Phe-Val-Phe-Ile-Phe-Thr-Tyr-Gly-Glu-Leu-Ala-
Arg-NH$_2$ (SEQ ID NO:145);
(Me$_2$N)-Phe-Val-Phe-Ile-Phe-Thr-Tyr-Gly-Glu-Leu-Ala-
Arg-NH$_2$ (SEQ ID NO:146);
(N-Me)-Phe-Val-D-Phe-Ile-Phe-Thr-Tyr-Gly-Glu-Leu-Gln-
D-Arg-NH$_2$ (SEQ ID NO:147);
(Me$_2$N)-Phe-Val-D-Phe-Ile-Phe-Thr-Tyr-Gly-Glu-Leu-Gln-
D-Arg-NH$_2$ (SEQ ID NO:148);
(N-Me)-Phe-Val-Phe-Ile-Phe-Thr-Tyr-Gly-Glu-Leu-Gln-D-
Arg-NH$_2$ (SEQ ID NO:149);
(Me$_2$N)-Phe-Val-Phe-Ile-Phe-Thr-Tyr-Gly-Glu-Leu-Gln-D-
Arg-NH$_2$ (SEQ ID NO:150);
(N-Me)-Phe-Val-D-Phe-Ile-Phe-Thr-Tyr-Gly-Glu-Leu-Ala-
D-Arg-NH$_2$ (SEQ ID NO:151);
(Me$_2$N)-Phe-Val-D-Phe-Ile-Phe-Thr-Tyr-Gly-Glu-Leu-Ala-
D-Arg-NH$_2$ (SEQ ID NO:152);
(N-Me)-Phe-Val-Phe-Ile-Phe-Thr-Tyr-Gly-Glu-Leu-Ala-D-
Arg-NH$_2$ (SEQ ID NO:153);
(Me$_2$N)-Phe-Val-Phe-Ile-Phe-Thr-Tyr-Gly-Glu-Leu-Ala-D-
Arg-NH$_2$ (SEQ ID NO:154);
and their pharmaceutically acceptable addition salts. In a most preferred embodiment, the compounds of the present invention are selected from the group consisting of
H-Phe-Val-Phe-Ile-Phe-Thr-Tyr-Gly-Glu-Leu-Gln-Arg-
Leu-Glu-Lys-Glu-Arg-Asn-Lys-Gly-Gln-OH (SEQ ID NO:9);
H-Phe-Val-Phe-Ile-Phe-Thr-Tyr-Gly-Glu-Leu-Gln-Arg-
Leu-Glu-Lys-Glu-Arg-Asn-Lys-Gly-Gln-NH$_2$ (SEQ ID NO:10);
H-Phe-Val-D-Phe-Ile-Phe-Thr-Tyr-Gly-Glu-Leu-Gln-Arg-
Leu-Glu-Lys-Glu-Arg-Asn-Lys-Gly-Gln-OH (SEQ ID NO:11);
H-Phe-Val-D-Phe-Ile-Phe-Thr-Tyr-Gly-Glu-Leu-Gln-Arg-
Leu-Glu-Lys-Glu-Arg-Asn-Lys-Gly-Gln-NH$_2$ (SEQ ID NO:12);
(N-Me)-Phe-Val-Phe-Ile-Phe-Thr-Tyr-Gly-Glu-Leu-Gln-
Arg-Leu-Gln-OH (SEQ ID NO:15);
(Me$_2$N)-Phe-Val-Phe-Ile-Phe-Thr-Tyr-Gly-Glu-Leu-Gln-
Arg-Leu-Gln-OH (SEQ ID NO:16);
(N-Me)-Phe-Val-Phe-Ile-Phe-Thr-Tyr-Gly-Glu-Leu-Gln-
Arg-Leu-Gln-NH$_2$ (SEQ ID NO:32);
(Me$_2$N)-Phe-Val-Phe-Ile-Phe-Thr-Tyr-Gly-Glu-Leu-Gln-
Arg-Leu-Gln-NH$_2$ (SEQ ID NO:33);
(N-Me)-Phe-Val-D-Phe-Ile-Phe-Thr-Tyr-Gly-Glu-Leu-Gln-
Arg-Leu-Gln-OH (SEQ ID NO:58);
(Me$_2$N)-Phe-Val-D-Phe-Ile-Phe-Thr-Tyr-Gly-Glu-Leu-Gln-
Arg-Leu-Gln-OH (SEQ ID NO:59);
(N-Me)-Phe-Val-D-Phe-Ile-Phe-Thr-Tyr-Gly-Glu-Leu-Gln-
Arg-Leu-Gln-NH$_2$ (SEQ ID NO:69);
(Me$_2$N)-Phe-Val-D-Phe-Ile-Phe-Thr-Tyr-Gly-Glu-Leu-Gln-
Arg-Leu-Gln-NH$_2$ (SEQ ID NO:70);
(N-Me)-Phe-Val-D-Phe-Ile-Phe-Thr-Tyr-Gly-Glu-Leu-Gln-
Arg-Leu-D-Gln-NH$_2$ (SEQ ID NO:87);
(Me$_2$N)-Phe-Val-D-Phe-Ile-Phe-Thr-Tyr-Gly-Glu-Leu-Gln-
Arg-Leu-D-Gln-NH$_2$ (SEQ ID NO:88);
(N-Me)-Phe-Val-Phe-Ile-Phe-Thr-Tyr-Gly-Glu-Leu-G
n-Arg-Leu-D-Gln-NH$_2$ (SEQ ID NO:89);
(Me$_2$N)-Phe-Val-Phe-Ile-Phe-Thr-Tyr-Gly-Glu-Leu-Gln-
Arg-Leu-D-Gln-NH$_2$ (SEQ ID NO:90);

(N-Me)-Phe-Val-D-Phe-Ile-Phe-Thr-Tyr-Gly-Glu-Leu-Gln-D-Arg-Leu-Gln-NH$_2$ (SEQ ID NO:91);
(Me$_2$N)-Phe-Val-D-Phe-Ile-Phe-Thr-Tyr-Gly-Glu-Leu-Gln-D-Arg-Leu-Gln-NH$_2$ (SEQ ID NO:92);
(N-Me)-Phe-Val-Phe-Ile-Phe-Thr-Tyr-Gly-Glu-Leu-Gln-D-Arg-Leu-Gln-NH$_2$ (SEQ ID NO:93);
(Me$_2$N)-Phe-Val-Phe-Ile-Phe-Thr-Tyr-Gly-Glu-Leu-Gln-D-Arg-Leu-Gln-NH$_2$ (SEQ ID NO:94);
(N-Me)-Phe-Val-D-Phe-Ile-Phe-Thr-Tyr-Gly-Glu-Leu-Gln-Arg-Leu-Lys-NH$_2$ (SEQ ID NO:95);
(Me$_2$N)-Phe-Val-D-Phe-Ile-Phe-Thr-Tyr-Gly-Glu-Leu-Gln-Arg-Leu-Lys-NH$_2$ (SEQ ID NO:96);
(N-Me)-Phe-Val-Phe-Ile-Phe-Thr-Tyr-Gly-Glu-Leu-Gln-Arg-Leu-Lys-NH$_2$ (SEQ ID NO:97);
(Me$_2$N)-Phe-Val-Phe-Ile-Phe-Thr-Tyr-Gly-Glu-Leu-Gln-Arg-Leu-Lys-NH$_2$ (SEQ ID NO:98);
(N-Me)-Phe-Val-D-Phe-Ile-Phe-Thr-Tyr-Gly-Glu-Leu-Gln-D-Arg-Leu-Lys-NH$_2$ (SEQ ID NO:99);
(Me$_2$N)-Phe-Val-D-Phe-Ile-Phe-Thr-Tyr-Gly-Glu-Leu-Gln-D-Arg-Leu-Lys-NH$_2$(SEQ ID NO:100);
(N-Me)-Phe-Val-Phe-Ile-Phe-Thr-Tyr-Gly-Glu-Leu-Gln-D-Arg-Leu-Lys-NH$_2$ (SEQ ID NO:101);
(Me$_2$N)-Phe-Val-Phe-Ile-Phe-Thr-Tyr-Gly-Glu-Leu-Gln-D-Arg-Leu-Lys-NH$_2$ (SEQ ID NO:102);
(N-Me)-Phe-Val-D-Phe-Ile-Phe-Thr-Tyr-Gly-Glu-Leu-Gln-Arg-Leu-D-Lys-NH$_2$ (SEQ ID NO:103);
(Me$_2$N)-Phe-Val-D-Phe-Ile-Phe-Thr-Tyr-Gly-Glu-Leu-Gln-Arg-Leu-D-Lys-NH$_2$ (SEQ ID NO:104);
(N-Me)-Phe-Val-Phe-Ile-Phe-Thr-Tyr-Gly-Glu-Leu-Gln-Arg-Leu-D-Lys-NH$_2$ (SEQ ID NO:105);
(Me$_2$N)-Phe-Val-Phe-Ile-Phe-Thr-Tyr-Gly-Glu-Leu-Gln-Arg-Leu-D-Lys-NH$_2$ (SEQ ID NO:106);
(N-Me)-Phe-Val-D-Phe-Ile-Phe-Thr-Tyr-Gly-Glu-Leu-Gln-D-Arg-Leu-D-Lys-NH$_2$(SEQ ID NO:107);
(Me$_2$N)-Phe-Val-D-Phe-Ile-Phe-Thr-Tyr-Gly-Glu-Leu-Gln-D-Arg-Leu-D-Lys-NH$_2$(SEQ ID NO:108);
(N-Me)-Phe-Val-Phe-Ile-Phe-Thr-Tyr-Gly-Glu-Leu-Gln-D-Arg-Leu-D-Lys-NH$_2$ (SEQ ID NO:109);
(Me$_2$N)-Phe-Val-Phe-Ile-Phe-Thr-Tyr-Gly-Glu-Leu-Gln-D-Arg-Leu-D-Lys-NH$_2$ (SEQ ID NO:110);
(N-Me)-Phe-Val-D-Phe-Ile-Phe-Thr-Tyr-Gly-Glu-Leu-Gln-D-Arg-Leu-D-Gln-NH$_2$ (SEQ ID NO:111);
(Me$_2$N)-Phe-Val-D-Phe-Ile-Phe-Thr-Tyr-Gly-Glu-Leu-Gln-D-Arg-Leu-D-Gln-NH$_2$(SEQ ID NO:112);
(N-Me)-Phe-Val-Phe-Ile-Phe-Thr-Tyr-Gly-Glu-Leu-Gln-D-Arg-Leu-D-Gln-NH$_2$ (SEQ ID NO:113);
(Me$_2$N)-Phe-Val-Phe-Ile-Phe-Thr-Tyr-Gly-Glu-Leu-Gln-D-Arg-Leu-D-Gln-NH$_2$ (SEQ ID NO:114);
(N-Me)-Phe-Val-D-Phe-Ile-Phe-Thr-Tyr-Gly-Glu-Leu-Ala-Arg-Leu-Gln-NH$_2$ (SEQ ID NO:115);
(Me$_2$N)-Phe-Val-D-Phe-Ile-Phe-Thr-Tyr-Gly-Glu-Leu-Ala-Arg-Leu-Gln-NH$_2$ (SEQ ID NO:116);
(N-Me)-Phe-Val-Phe-Ile-Phe-Thr-Tyr-Gly-Glu-Leu-Ala-Arg-Leu-Gln-NH$_2$ (SEQ ID NO:117);
(Me$_2$N)-Phe-Val-Phe-Ile-Phe-Thr-Tyr-Gly-Glu-Leu-Ala-Arg-Leu-Gln-NH$_2$ (SEQ ID NO:118);
(N-Me)-Phe-Val-D-Phe-Ile-Phe-Thr-Tyr-Gly-Glu-Leu-Ala-Arg-Leu-D-Gln-NH$_2$ (SEQ ID NO:119);
(Me$_2$N)-Phe-Val-D-Phe-Ile-Phe-Thr-Tyr-Gly-Glu-Leu-Ala-Arg-Leu-D-Gln-NH$_2$ (SEQ ID NO:120);
(N-Me)-Phe-Val-Phe-Ile-Phe-Thr-Tyr-Gly-Glu-Leu-Ala-Arg-Leu-D-Gln-NH$_2$ (SEQ ID NO:121);
(Me$_2$N)-Phe-Val-Phe-Ile-Phe-Thr-Tyr-Gly-Glu-Leu-Ala-Arg-Leu-D-Gln-NH$_2$ (SEQ ID NO:122);
(N-Me)-Phe-Val-D-Phe-Ile-Phe-Thr-Tyr-Gly-Glu-Leu-Ala-D-Arg-Leu-Gln-NH$_2$ (SEQ ID NO:123);
(Me$_2$N)-Phe-Val-D-Phe-Ile-Phe-Thr-Tyr-Gly-Glu-Leu-Ala-D-Arg-Leu-Gln-NH$_2$ (SEQ ID NO:124);
(N-Me)-Phe-Val-Phe-Ile-Phe-Thr-Tyr-Gly-Glu-Leu-Ala-D-Arg-Leu-Gln-NH$_2$ (SEQ ID NO:125);
(Me$_2$N)-Phe-Val-Phe-Ile-Phe-Thr-Tyr-Gly-Glu-Leu-Ala-D-Arg-Leu-Gln-NH$_2$ (SEQ ID NO:126);
(N-Me)-Phe-Val-D-Phe-Ile-Phe-Thr-Tyr-Gly-Glu-Leu-Ala-D-Arg-Leu-D-Gln-NH$_2$(SEQ ID NO:127);
(Me$_2$N)-Phe-Val-D-Phe-Ile-Phe-Thr-Tyr-Gly-Glu-Leu-Ala-D-Arg-Leu-D-Gln-NH$_2$ (SEQ ID NO:128);
(N-Me)-Phe-Val-Phe-Ile-Phe-Thr-Tyr-Gly-Glu-Leu-Ala-D-Arg-Leu-D-Gln-NH$_2$ (SEQ ID NO:129);
(Me$_2$N)-Phe-Val-Phe-Ile-Phe-Thr-Tyr-Gly-Glu-Leu-Ala-D-Arg-Leu-D-Gln-NH$_2$ (SEQ ID NO:130);
(N-Me)-Phe-Val-D-Phe-Ile-Phe-Thr-Tyr-Gly-Glu-Leu-Ala-D-Arg-Leu-Lys-NH$_2$ (SEQ ID NO:131);
(Me$_2$N)-Phe-Val-D-Phe-Ile-Phe-Thr-Tyr-Gly-Glu-Leu-Ala-D-Arg-Leu-Lys-NH$_2$ (SEQ ID NO:132);
(N-Me)-Phe-Val-Phe-Ile-Phe-Thr-Tyr-Gly-Glu-Leu-Ala-D-Arg-Leu-Lys-NH$_2$ (SEQ ID NO:133);
(Me$_2$N)-Phe-Val-Phe-Ile-Phe-Thr-Tyr-Gly-Glu-Leu-Ala-D-Arg-Leu-Lys-NH$_2$ (SEQ ID NO:134);
(N-Me)-Phe-Val-D-Phe-Ile-Phe-Thr-Tyr-Gly-Glu-Leu-Ala-D-Arg-Leu-D-Lys-NH$_2$ (SEQ ID NO:135);
(Me$_2$N)-Phe-Val-D-Phe-Ile-Phe-Thr-Tyr-Gly-Glu-Leu-Ala-D-Arg-Leu-D-Lys-NH$_2$ (SEQ ID NO:136);
(N-Me)-Phe-Val-Phe-Ile-Phe-Thr-Tyr-Gly-Glu-Leu-Ala-D-Arg-Leu-D-Lys-NH$_2$ (SEQ ID NO:137);
(Me$_2$N)-Phe-Val-Phe-Ile-Phe-Thr-Tyr-Gly-Glu-Leu-Ala-D-Arg-Leu-D-Lys-NH$_2$ (SEQ ID NO:138);
(N-Me)-Phe-Val-D-Phe-Ile-Phe-Thr-Tyr-Gly-Glu-Leu-Gln-Arg-NH$_2$ (SEQ ID NO:139);
(Me$_2$N)-Phe-Val-D-Phe-Ile-Phe-Thr-Tyr-Gly-Glu-Leu-Gln-Arg-NH$_2$ (SEQ ID NO:140);
(N-Me)-Phe-Val-Phe-Ile-Phe-Thr-Tyr-Gly-Glu-Leu-Gln-Arg-NH$_2$ (SEQ ID NO:141);
(Me$_2$N)-Phe-Val-Phe-Ile-Phe-Thr-Tyr-Gly-Glu-Leu-Gln-Arg-NH$_2$ (SEQ ID NO:142);
(N-Me)-Phe-Val-D-Phe-Ile-Phe-Thr-Tyr-Gly-Glu-Leu-Ala-Arg-NH$_2$ (SEQ ID NO:143);
(Me$_2$N)-Phe-Val-D-Phe-Ile-Phe-Thr-Tyr-Gly-Glu-Leu-Ala-Arg-NH$_2$ (SEQ ID NO;144);
(N-Me)-Phe-Val-Phe-Ile-Phe-Thr-Tyr-Gly-Glu-Leu-Ala-Arg-NH$_2$ (SEQ ID NO:145);
(Me$_2$N)-Phe-Val-Phe-Ile-Phe-Thr-Tyr-Gly-Glu-Leu-Ala-Arg-NH$_2$ (SEQ ID NO:146);
(N-Me)-Phe-Val-D-Phe-Ile-Phe-Thr-Tyr-Gly-Glu-Leu-Gln-D-Arg-NH$_2$ (SEQ ID NO:147);
(Me$_2$N)-Phe-Val-D-Phe-Ile-Phe-Thr-Tyr-Gly-Glu-Leu-Gln-D-Arg-NH$_2$ (SEQ ID NO:148);
(N-Me)-Phe-Val-Phe-Ile-Phe-Thr-Tyr-Gly-Glu-Leu-Gln-D-Arg-NH$_2$ (SEQ ID NO:149);
(Me$_2$N)-Phe-Val-Phe-Ile-Phe-Thr-Tyr-Gly-Glu-Leu-Gln-D-Arg-NH$_2$ (SEQ ID NO;150);
(N-Me)-Phe-Val-D-Phe-Ile-Phe-Thr-Tyr-Gly-Glu-Leu-Ala-D-Arg-NH$_2$ (SEQ ID NO:151);
(Me$_2$N)-Phe-Val-D-Phe-Ile-Phe-Thr-Tyr-Gly-Glu-Leu-Ala-D-Arg-NH$_2$ (SEQ ID NO:152);
(N-Me)-Phe-Val-Phe-Ile-Phe-Thr-Tyr-Gly-Glu-Leu-Ala-D-Arg-NH$_2$ (SEQ ID NO:153);
(Me$_2$N)-Phe-Val-Phe-Ile-Phe-Thr-Tyr-Gly-Glu-Leu-Ala-D-Arg-NH$_2$ (SEQ ID NO:154);
and their pharmaceutically acceptable addition salts.

The compounds of the present invention can be prepared by various methods known in the art such as by solid phase peptide synthesis or by classical solution phase synthesis. In the solid phase method, the peptide chain is sequentially constructed using a resin support, typically a polystyrene based, polyhipe based, or a polyacrylamide/Kieselguhr composite resin. The growing peptide chain is tethered to the resin support by a suitable, acid-labile molecular linker, such as hydroxymethylphenylacetamidomethyl (PAM), 4-methylbenzhydrylamino (MBHA), or hydroxymethylphenoxyacetoxy (HMPA) moieties. The peptide chain can then be cleaved from the linker, and thus the resin support, through acidolysis employing hydrogen fluoride, trifluoroacetic acid (TFA), trifluoromethanesulfonic acid (TFMSA), and the like.

Whether the gastrointestinal motor inhibitory polypeptides of this invention are prepared by solid phase or solution phase methods, the basic synthetic approach involves coupling of amino acid subunits through reaction of the carboxyl moiety of one suitably protected amino acid or peptide fragment with the amino group of another suitably protected amino acid or peptide fragment to form a new amide bond. In order to effect the coupling reaction, the carboxyl moiety must be activated. Activation is accomplished through the use of standard coupling reagents such as DCC, DIC, EDCC, BOP, HBTU, or PyBrOP. Except in the case of PyBrOP, an equimolar amount of HOBt may be added to suppress racemization of the activated amino acid component. Bases such as NMM, DIEA, or TEA may be used in those cases where it is necessary to employ the carboxylate salt of the corresponding amino acid for activation.

Alternatively, the peptides of this invention can be synthesized by coupling the active esters of the component amino acids. Such active esters include, for example, a pentachlorophenyl ester, a pentafluorophenyl ester, a p-nitrophenyl ester, and the like.

During the preparation of the peptides of this invention, other reactive functionalities of the amino acid components must be blocked with appropriate protecting groups. In general, the identity of the α-amino protecting group dictates what type of side-chain protecting groups must be employed. For example, in the case where the α-amino group is protected as its Boc derivative, side-chain protection is usually accomplished with ester, ether, or urethane derivatives of benzyl alcohol. Ester and ether derivatives of cyclohexanol have also been used with some success. In contrast, when the α-amino group is protected as its Fmoc derivative, side chain functionality is generally protected as ester, ether, or urethane derivatives of t-butanol. Of course, alternative combinations of protecting groups may be employed especially when the peptides of this invention are synthesized by solution phase methodology.

Removal of the Fmoc α-amino protecting group may be readily accomplished with a base, typically piperidine. The side chain protecting groups can be removed by treatment with TFA in the presence of an appropriate carbonium ion scavenger, which also cleaves the bond between the C-terminus of the peptide and the resin linker. The Boc protecting group is generally removed by treatment with dilute TFA. Following TFA cleavage, however, the α-amino group is present as its TFA salt. In order to make the α-amino group of the growing peptide chain reactive toward the next amino acid derivative, the resin-bound peptide is neutralized with a base such as TEA or DIEA. Strong acid, such as hydrofluoric acid or TFMSA, containing suitable scavengers is then used to deprotect the amino acid side-chains and to cleave the peptide from the resin support.

The compounds of the present invention while effective in the form of the free base may be formulated and administered in the form of pharmaceutically acceptable acid addition salts for purposes of stability, convenience of crystallization, increased solubility and the like. These acid addition salts are formed by conventional methods from suitable inorganic or organic acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic acid, and the like. Preferably, the acid addition salts are those prepared from hydrochloric acid, acetic acid, or succinic acid.

The compounds of the present invention can be combined with a pharmaceutically acceptable carrier to provide a pharmaceutical composition. Suitable carriers for the subject compounds as the free base include propylene glycol-alcohol-water, isotonic water, sterile water for injection (USP), emulphor$^{TM}$-alcohol-water, cremophor-EL$^{TM}$ or other suitable carriers known to those skilled in the art.

Suitable carriers for the acid addition salts of the subject compounds include isotonic water, sterile water for injection (USP), alone or in combination with other solubilizing agents such as ethanol, propylene glycol, or other conventional solubilizing agents known to those skilled in the art. A preferred carrier is an isotonic aqueous solution of the inventive compound.

The compounds of the present invention can be administered to mammals, e.g., animals or humans, in amounts effective to provide the desired gastrointestinal motor inhibitory activity. Since the activity of the compounds and the degree of the desired therapeutic effect vary, the dosage level of the compound employed will also vary. The actual dosage administered will also be determined by such generally recognized factors as the body weight of the patient and the individual hypersensitiveness of the particular patient. Thus, the unit dosage for a particular patient (man) can vary from as low as about 0.1 μg per kg of body weight, which the practitioner may titrate to the desired effect. A preferred minimum dose for titration is 1 μg/kg body weight.

The compounds of the present invention can be administered by recognized parenteral mutes, in the form of sterile solutions or suspensions, in the carriers previously described. These preparations should contain at least about 0.1%, by weight, of the inventive compound but this amount may be varied to between about 0.1% and about 50%, by weight, of the inventive compound. The compounds of the present invention are preferably administered intravenously and the dosage used will generally be in the range from about 0.1 μg to about 500 mg, and preferably from about 1 μg to about 50 mg, per 70 kg body weight. This dosage may be administered from 1 to 4 times daily.

The sterile solutions or suspensions may also include the following adjuvants: a sterile diluent, such as water for injection, saline solution, fixed oils, polyethylene glycol, glycerine, propylene glycol, or other synthetic solvent; antibacterial agents, such as benzyl alcohol or methyl paraben; antioxidants, such as ascorbic acid or sodium metabisulfite; chelating agents, such as ethylenediaminetetraacetic acid (EDTA); buffers, such as acetates, citrates or phosphates; and agents for the adjustment of tonicity, such as sodium chloride or dextrose. The parenteral preparations may be enclosed in ampules, disposable syringes, or multiple dosage vials made of glass or plastic.

Throughout this application, various publications have been referenced. The disclosures in these publications are incorporated herein by reference in order to more fully describe the state of the art.

The present invention is further illustrated by the following examples which are presented for purposes of demonstrating, but not limiting, the preparation of the compounds and compositions of this invention.

EXAMPLE 1

[3-Phenylalanine, 13-leucine]motilin (Porcine), Pentakis-trifluoroacetate Salt

H-Phe-Val-Phe-Ile-Phe-Thr-Tyr-Gly-Glu-Leu-Gln-Arg-Leu-Gln-Glu-Lys-Glu-Arg-Asn-Lys-Gly-Gln-OH

The peptide was synthesized on 2.0 g. of Fmoc-L-Gln-(Mbh)PepSyn KA resin (0.08 mequiv/g) by solid phase continuous flow techniques employing a MilliGen Model 9050 peptide synthesizer. All residues were coupled as Pfp esters of the Fmoc amino acids in the presence of HOBt, except for Thr which was the ODhbt ester. The side chain protection was as follows: Arg(Mtr), Glu(OtBu), Lys(Boc), Tyr(tBu), and Thr(tBu). Asn and Gln were left unprotected. A four-fold molar excess of the Fmoc amino acid OPfp/HOBt in DMF was used for coupling. Coupling efficiency was monitored by the Kaiser test. Coupling times ranged from 1–4 hours. After each coupling cycle, removal of the Fmoc-α-amino protecting group was accomplished with 20% piperidine in DMF. Following synthesis, the resin-bound peptide was washed with DCM and dried under vacuum overnight. Deblocking and cleavage of the peptide from the resin was performed at room temperature by shaking with anhydrous TFA containing 5% thioanisole, 3% ethanedithiol, and 2% anisole (20 ml. total) for 8 hours. The cleavage solution then was added dropwise to 250 ml. cold ether and the precipitated peptide collected by filtration to obtain 370 mg (70%) of the title peptide as a white powder. Peptide purification was achieved in three runs (typical load=125 mg per run) by HPLC on a Waters Delta-Prep 3000 (Waters Associates) using two C-18 columns in series (250×20 mm, 15μ, Vydac). The solvent system was 0.1% TFA with a 30 minute gradient to 60% acetonitrile/40% TFA(0.1%) at 20 ml/min with UV detection at 220 nm. The purity of individual fractions was assessed by analytical HPLC (30 minute gradient, 100% TFA(0.1%) to 100% acetonitfile, 1 ml/min, 214 nm; $R_t$=16.22 min) and capillary zone electrophoresis. Pure fractions (>95%) were pooled and lyophilized to provide 145 mg (27%) of the title peptide as a flocculent white powder.

AAA: Asx 1.01 (1), Thr 0.84 (1), Glx 6.01 (6), Gly 2.05 (2), Val 0.97 (1), Ile 0.92 (1), Leu 2.02 (2), Tyr 0.99 (1), Phe 2.95 (3), Lys 2.13 (2), Arg 2.00 (2). FAB-MS: $(M+H)^+$ calcd 2732, found 2732.

EXAMPLE 2

[3-Phenylalanine]motilin-(1-12)-peptide Amide (Porcine), Bis-trifluoroacetate Salt
H-Phe-Val-Phe-Ile-Phe-Thr-Tyr-Gly-Glu-Leu-Gln-Arg-NH$_2$ The peptide was synthesized on 1.0 g. of MBHA resin (0.27 mequiv/g) using a MilliGen Model 9600 peptide synthesizer. All Boc amino acids were coupled following preactivation with an equimolar amount of DIC in DMF/DCM. Boc-L-Gln-OH was preactivated in the presence of 1.5 equivalents of HOBt to suppress dehydration of the amide side chain. The side chain protection was as follows: Arg(Tos), Glu(OBzl), Tyr(2-Br-Cbz), and Thr(Bzl). A 6.67-fold molar excess of the Boc amino acid was used for coupling. Coupling strategy was determined by the Analysis Expert System in the Milligen Biodrive v 1.05 software package. Protocols were as follows: Arg$^{12}$ (2 hr, double couple); Gln$^{11}$ (2 hr, single couple); Leu$^{10}$ (2 hr, single couple): Glu$^9$ (2 hr, single couple); Gly$^8$ (2 hr, single couple); Tyr$^7$ (2 hr, single couple): Thr$^6$ (2 hr, single couple); Phe$^5$ (2 hr, double couple); Ile$^4$ (2 hr, double couple): Phe$^3$ (2 hr, double couple); Val$^2$ (2 hr, double couple); Phe$^1$ (2 hr, double couple). Coupling efficiency was monitored by the Kaiser test. After each cycle, removal of the Boc-α-amino protecting group was accomplished with TFA/anisole/DCM (45:2.5:52.5). The peptide was convened to its free base by washing with 10% DIEA in DCM. Following synthesis, the resin-bound peptide was dried under vacuum overnight. Deblocking and cleavage of the peptide from the resin was performed at –5° C. for 2 hours by stirring the resin with anhydrous HF containing 8.3% dimethylsulfide and 8.3% anisole (10 ml. total). Following evaporation of tile cleavage solution, the residue was partitioned between ether (150 ml) and water (150 ml). The aqueous layer was washed several times with ether (4×150 ml) and lyophilized to provide the title peptide as a white powder. Peptide purification was achieved in two runs (typical load=115 mg per run) by HPLC on a Waters Delta-Prep 3000 (Waters Associates) using two C-18 columns in series (250×20 mm, 15μ, Vydac). The solvent system was 0.1% TFA with a 30 minute gradient to 60% acetonitrile/40% TFA(0.1%) at 20 ml/min with UV detection at 220 nm. The purity of individual fractions was assessed by analytical HPLC (30 minute gradient, 100% TFA(0.1%) to 100% acetonitrile, 1 ml/min, 214 nm; $R_t$=17.05 min) and capillary zone electrophoresis. Pure fractions (>95%) were pooled and lyophilized to provide 97 mg (21%) of the title peptide as a flocculent white powder.

AAA: Thr 0.95 (1), Glx 2.05 (2), Gly 1.02 (1), Val 0.85 (1), Ile 0.95 (1), Leu 1.06 (1), Tyr 1.03 (1), Phe 3.01 (3), Arg 1.06 (1). FAB-MS: $(M+H)^+$ calcd 1519, found 1519.

EXAMPLE 3

[1-N-Methylphenylalanine, 3-phenylalanine, 13-leucine] motilin-(1-14)-peptide (Porcine), Bis-trifluoroacetate Salt
(N-Me)-Phe-Val-Phe-Ile-Phe-Thr-Tyr-Gly-Glu-Leu-Gln-Arg-Leu-Gln-OH The peptide was synthesized on 0.9 g. of Fmoc-L-Gln-(Trt)PAC resin (0.28 mequiv/g) by solid phase continuous flow techniques employing a MilliGen Model 9050 peptide synthesizer. The resin was mixed with 5.4 g of glass beads (acid washed, 150–212 microns), dry-packed into a continuous flow column, and swelled with DMF for 1 hr prior to use. Fmoc-MePhe-OH was coupled by preactivation with BOP and HOBt (1:1:1) in the presence of 0.6M NMM in DMF. Fmoc-L-Thr-OH was coupled as its ODhbt ester in the presence of HOBt. All other residues were coupled as Pfp esters of the Fmoc amino acids in the presence of HOBt. The side chain protection was as follows: Arg(Mtr), Glu(OtBu), Tyr(tBu), and Thr(tBu). Gln was left unprotected. A four-fold molar excess of the Fmoc amino acid derivative in DMF was used for coupling. Coupling efficiency was monitored by the Kaiser test. Typical coupling times ranged from 1–4 hours. After each cycle, removal of the Fmoc-α-amino protecting group was accomplished with 20% piperidine in DMF. Following synthesis, the resin-bound peptide was washed with DCM and dried under vacuum overnight. Deblocking and cleavage of the peptide from the resin was performed at room temperature by shaking with anhydrous TFA containing 5% thioanisole, 3% ethanedithiol, and 2% anisole (20 ml. total) for 8 hours. The cleavage solution then was added dropwise to 250 ml. cold ether and the precipitated peptide collected by filtration to obtain the title peptide as a white powder. Peptide purification was achieved in three runs (typical load=100 mg per run) by HPLC on a Waters Delta-Prep 3000 (Waters Associates) using two C-18 columns in series (250×20 mm, 15μ, Vydac). The solvent system was 0.1% TFA with a 30 minute gradient to 60% acetonitrile/40% TFA(0.1%) at 20 ml/min with UV detection at 220 nm. The purity of individual fractions was assessed by analytical HPLC (30 minute gradient, 100% TFA(0.1%) to 100% acetonitrile, 1 ml/min, 214 nm; $R_t$=17.99 min) and capillary zone electrophoresis. Pure fractions (>95%) were pooled and lyophilized to provide 86 mg (18%) of the title peptide as a flocculent white powder.

AAA: Thr 0.87 (1), Glx 3.13 (3), Gly 1.13 (1), Val 0.75 (1), Ile 0.96 (1), Leu 2.10 (2), Tyr 0.99 (1), Phe 1.97 (2), Arg 1.03 (1). FAB-MS: $(M+H)^+$ calcd 1775, found 1775.

EXAMPLE 4

Determination of Motilin Receptor Binding Affinity

The motilin receptor binding affinity of the peptides of this invention was determined by using the general procedure of Bormans, Peelers and Vantrappen, Regul. Pept., 15, 143–153 (1986). The ability of the peptides to displace [$^{125}$I-Tyr$^7$,Nle$^{13}$]motilin(porcine) bound to rabbit antral smooth muscle membranes, was determined by testing twice, each time in duplicate, at concentrations ranging from $10^{-11}$ to $10^{-4}$M. The concentration displacing 50% of the label (IC$_{50}$) was determined by fitting the data to the equation describing displacement, assuming a single class of motilin receptors to which labeled and non-labeled motilin bind with equal affinity and non-cooperatively. Fitting was performed using the iterative least-squares procedure of the SAS-software package (SAS Institute, Inc., Cary, N.C., U.S.A.). From a large series of control experiments the dissociation constant of motilin itself was calculated as 0.75 nM (pK$_d$=9.12), and this value was used for all calculations. The concentration displacing 50% of the label is expressed using its negative logarithm (pIC$_{50}$).

EXAMPLE 5

Rabbit Duodenal Smooth Muscle Strip Tissue Bath Assay

The contractile response of segments of rabbit duodenum was determined isotonically in the tissue bath according to the procedure of Depoortere et al., J. Gastrointestinal Motility, 1, 150–159 (1989). The experimental protocol consisted of an equilibration period of 1 hour: a challenge with $10^{-4}$M acetylcholine followed by a wash-out period; a cumulative dose-response curve of a compound with, at the end, the addition of $10^{-7}$M motilin; and finally $10^{-4}$M acetylcholine. If the final response to $10^{-4}$M acetylcholine differed by more than 5% from the initial response, the results were discarded. The compounds were tested in the concentration range $10^{-11}$ to $10^{-4}$M. The point corresponding to 50% of the maximal response to motilin (E$_{max}$) was determined by fitting the equation E=E$_{max}$ (1+EC$_{50}$/[L]) through the data points. For weakly active compounds 90% of the response to $10^{-7}$M motilin was used as E$_{max}$. The dose giving 50% of the response is expressed using its negative logarithm (pEC$_{50}$).

EXAMPLE 6

Motilin Receptor Antagonism

To determine motilin receptor antagonism, the contractile response of segments of rabbit duodenum to motilin was determined isotonically in the tissue bath in the presence of a fixed concentration of the compound of interest. The experimental protocol consisted of an equilibration period of 1 hour; a challenge with $10^{-4}$M acetylcholine followed by a wash-out period; a cumulative motilin dose-response curve in the presence of the motilin receptor antagonist; and finally a challenge with $10^{-4}$M acetylcholine. If the final response to $10^{-4}$M acetylcholine differed by more than 5% from the initial response, the results were discarded. The point corresponding to 50% of the maximal response to motilin (E$_{max}$) was determined by fitting the equation $$E=E_{max} (1+EC_{50}/[L])$$

through the data points. The dose of motilin giving 50% of the response is expressed using its negative logarithm (pEC$_{50}$). Compounds of interest were tested at concentrations of $10^{-8}$ to $10^{-5}$M.

For example, in the presence of $10^{-6}$M [Phe$^3$, Leu$^{13}$] pMOT(1-14) the dose-response curve of motilin was shifted by about one log unit. Thus the pEC$_{50}$ was 7.26$\pm$0.21 as compared to the control value of 8.33$\pm$0.17. [Phe$^3$, Leu$^{13}$] pMOT(1-14) at $10^{-5}$M completely blocked the full contractile response to motilin. The competitive nature of the interaction was confirmed by Schild-analysis (slope: 0.86$\pm$0.06).

| Motilin Receptor Antagonists in Binding and in Contractility Experiments | | |
|---|---|---|
| Compound | pEC50 | pIC50 |
| [Phe$^3$,Leu$^{13}$]pMOT | <4.5 | 9.11 |
| [Ile$^3$, Leu$^{13}$]pMOT | <4.5 | 7.82 |
| [Phe$^3$, Leu$^{13}$]pMOT(1-14) | <4.5 | 7.79 |
| [Leu$^3$, Leu$^{13}$]pMOT(1-14) | <4.5 | 6.75 |
| [p-I-Phe$^3$, Leu$^{13}$]pMOT(1-14) | <4.5 | 7.36 |
| [Thi$^3$, Leu$^{13}$]pMOT(1-14) | <4.5 | 7.59 |
| [Cha$^3$, Leu$^{13}$]pMOT(1-14) | <4.5 | 7.68 |
| [2-Nal$^3$, Leu$^{13}$]pMOT(1-14) | <4.5 | 7.56 |
| [D-Phe$^3$, Leu$^{13}$]pMOT(1-14) | <4.5 | 8.09 |
| [Pal$^3$, Leu$^{13}$]pMOT(1-14) | <4.5 | 6.80 |
| [Phe$^3$, D-Arg$^{12}$, Leu$^{13}$]pMOT(1-14) | <4.5 | 7.09 |
| [Phe$^3$, Leu$^4$, Leu$^{13}$]pMOT(1-14) | <4.5 | 8.40 |
| [Phe$^3$, Ala$^5$, Leu$^{13}$]pMOT(1-14) | <4.5 | 7.80 |
| [Phe$^3$, Leu$^7$, Leu$^{13}$]pMOT(1-14) | <4.5 | 7.51 |
| [Phe$^3$, D-Ala$^8$, Leu$^{13}$]pMOT(1-14) | <4.5 | 7.31 |
| [Phe$^3$, Ala$^{11}$, Leu$^{13}$]pMOT(1-14) | <4.5 | 7.80 |
| [Leu$^2$, Phe$^3$, Leu$^{13}$]pMOT(1-14) | <4.5 | 7.47 |
| [Phe$^3$, Leu$^{13}$, Lys$^{14}$]pMOT(1-14) amide | <4.5 | 8.80 |
| [D-Phe$^1$, Phe$^3$, Leu$^{13}$]pMOT(1-14) | <4.5 | 6.64 |
| [Cha$^1$, Phe$^3$, Leu$^{13}$]pMOT(1-14) | <4.5 | 7.53 |
| [Phe$^3$pMOT(1-12) amide | <4.5 | 7.56 |
| [N—MePhe$^1$, Phe$^3$, Leu$^3$]pMOT(1-14) | <4.5 | 7.97 |
| [Phe$^3$, Cha$^5$, Leu$^{13}$]pMOT(1-14) | <4.5 | 7.60 |
| [Phe$^3$, Leu$^{13}$, D-Gln$^{14}$]pMOT(1-14) amide | <4.5 | 9.01 |

*pMOT = porcine motilin

While we have represented a number of embodiments of this invention, it is apparent that the basic construction can be altered to provide other embodiments which utilize the invention without departing from the spirit and scope of the invention. All such modifications and variations are intended to be included within the scope of the invention as defined in the appended claims rather than the specific embodiments which have been presented by way of example.

We claim:

1. Polypeptides having gastrointestinal motor inhibitory activity represented by the formula:

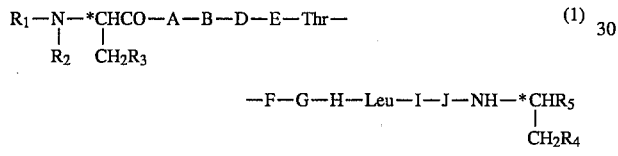

including optically active icomeric forms and the pharmaceutically acceptable acid addition salts thereof wherein:

A is the L-stereoisomer of a lipophilic aliphatic amino acid;

B is selected from the group consisting of phenylalanine, p-fluorophenylalanine, p-chlorophenylalanine, p-bromophenylalanine, p-iodophenylalanine, tyrosine, p-methaxyphenylalanine, 1-naphthylalanine, 2-naphthalalanine, tryptophan, β-2-thienylalanine, homophenylalanine, β-3-pyridylalanine, and cyclohexylalanine;

D is the L-stereoisomer of a lipophilic aliphatic amino acid;

E is the L-stereoisomer of an aromatic, aliphatic, or alicyclic amino acid;

F is the L-stereoisomer of an aromatic or heteroaromatic amino acid;

G is glycine or D-alanine;

H is L-glutamic acid or L-glutamine;

I is L-glutamine, L-glutamic acid, or L-alanine;

J is a direct bond between I and group —NH— or is selected from the group consisting of Z, Z-Leu, Z-Leu-Gln, Z-Leu-Gln-Glu (SEQ ID NO:2), Z-Leu-Gln-Glu-Lys (SEQ ID NO:3), Z-Leu-Gln-Glu-Lys-Glu (SEQ ID NO:4), Z-Leu-Gln-Glu-Lys-Glu-Arg (SEQ ID NO:5), Z-Leu-Gln-Glu-Lys-Glu-Arg-Asn (SEQ ID NO:6), Z-Leu-Gln-Glu-Lys-Glu-Arg-Asn-Lys (SEQ ID NO:7), and Z-Leu-Gln-Glu-Lys-Glu-Arg-Asn-Lys-Gly (SEQ ID NO:8), wherein Z is selected from the group consisting of arginine, D-arginine, D-homoarginine, D-lysine, D-ornithine, D-2,4-diaminobutyric acid, D-glutamine, D-asparagine, and D-alanine;

$R_1$ and $R_2$ are independently hydrogen or lower-alkyl;

$R_3$ is cycloalkyl or aryl which may be unsubstituted or substituted with one or more substituents selected from the group consisting of halogen, hydroxy, and lower-alkoxy;

$R_4$ is selected from the group consisting of —CH$_2$CONH$_2$, aminoalkyl groups containing from 1 to 3 carbon atoms, and guanidinoalkyl groups containing 2 or 3 carbon atoms;

$R_5$ is —COOH or —CONH$_2$; and the symbol * represents an asymmetric carbon atom which may be in the D or L configuration, and each lower-alkyl group contains from 1 to 4 carbon atoms, with the proviso that $R_4$ is —CH$_2$CONH$_2$ only when J is Z-Leu or Z-Leu-Gln-Glu-Lys-Glu-Arg-Asn-Lys-Gly (SEQ ID NO:8).

2. The polypeptide according to claim 1, wherein $(R_1)(R_2)$N—*CH(CH$_2$R$_3$)CO— is selected from the group consisting of L-phenylalanine, D-phenylalanine, L-cyclohexylalanine, and D-cyclohexylalanine.

3. The polypeptide according to claim 1, wherein the amino acid of A is selected from the group consisting of valine, isoleucine, leucine, norvaline, and norleucine.

4. The polypeptide according to claim 1, wherein the amino acid of B is D-phenylalanine or L-phenylalanine.

5. The polypeptide according to claim 1, wherein the amino acid of D is selected from the group consisting of isoleucine, valine, leucine, norvaline, and norleucine.

6. The polypeptide according to claim 1, wherein the amino acid of E is selected from the group consisting of phenylalanine, p-fluorophenylalanine, p-chlorophenylalanine, p-bromophenylalanine, p-iodophenylalanine, tyrosine, p-methoxyphenylalanine, 1-naphthylalanine, 2-naphthylalanine, leucine, alanine, and cyclohexylalanine.

7. The polypeptide according to claim 1, wherein the amino acid of F is selected from the group consisting of tyrosine, phenylalanine, p-methoxyphenylalanine, histidine, tryptophan, β-2-thienylalanine, and β-3-pyridylalanine.

8. The polypeptide according to claim 1, wherein the amino acid of I is L-glutamine or L-alanine.

9. The polypeptide according to claim 1, wherein J is a direct bond between I and group —NH—.

10. The polypeptide according to claim 1, wherein J is selected from the group consisting of Z-Leu, Z-Leu-Gln-Glu (SEQ ID NO:2), Z-LeuGln-Glu-Lys-Glu (SEQ ID NO:4), Z-Leu-Gln-Glu-Lys-Glu-Arg-Asn (SEQ ID NO:6), and Z-Leu-Gln-Glu-Lys-Glu-Arg-Asn-Lys-Gly (SEQ ID NO:8) and Z is selected from the group consisting of arginine, D-arginine, and D-glutamine.

11. The polypeptide according to claim 1, wherein $R_1$ is methyl.

12. The polypeptide according to claim 1, wherein $R_2$ is methyl.

13. The polypeptide according to claim 1, wherein $R_3$ is selected from the group consisting of cyclohexyl, phenyl, p-fluorophenyl, p-chlorophenyl, p-bromophenyl, p-iodophenyl, p-hydroxyphenyl, p-methoxyphenyl, 1-naphthyl, and 2-naphthyl.

14. The polypeptide according to claim 1, wherein $R_4$ is selected from the group consisting of —$CH_2CONH_2$, and aminoalkyl groups containing from 1 to 3 carbon atoms.

15. The polypeptide according to claim 1, wherein the group —NH*CH($CH_2R_4$)—$R_5$ is selected from the group consisting of arginine, D-arginine, lysine, D-lysine, D-ornithine, D-2,4-diaminobutyric acid, and D-homoarginine.

16. The polypeptide according to claim 1, wherein the polypeptide is
H-Phe-Val-Phe-Ile-Phe-Thr-Tyr-Gly-Glu-Leu-Gln-Arg-Leu-Glu-Lys-Glu-Arg-Asn-Lys-Gly-Gln-OH (SEQ ID NO:9)
and its pharmaceutically acceptable acid addition salts.

17. The polypeptide according to claim 1, wherein the polypeptide is
H-Phe-Val-D-Phe-Ile-Phe-Thr-Tyr-Gly-Glu-Leu-Gln-Arg-Leu-Glu-Lys-Glu-Arg-Asn-Lys-Gly-Gln-OH (SEQ ID NO:11)
and its pharmaceutically acceptable acid addition salts.

18. The polypeptide according to claim 1, wherein the polypeptide is
(N-Me)-Phe-Val-D-Phe-Ile-Phe-Thr-Tyr-Gly-Glu-Leu-Gln-Arg-Leu-Gln-$NH_2$ (SEQ ID NO:69)
and its pharmaceutically acceptable addition salts.

19. A method for treating a condition of increased basal level of gastrointestinal motor activity in a mammal which comprises administering to the mammal a therapeutically effective amount of a polypeptide represented by the formula:

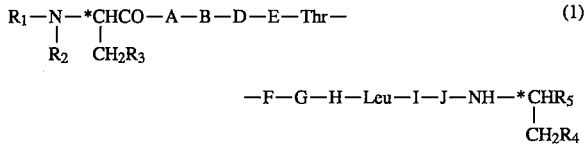

including optically active isomeric forms and the pharmaceutically acceptable acid addition salts thereof wherein:

A is the L-stereoisomer of a lipophilic aliphatic amino acid;

B is selected from the group consisting of phenylalanine, p-fluorophenylalanine, p-chlorophenyanine, p-bromophenylalanine, p-iodophenylalanine, tyrosine, p-methoxyphenylalanine, 1-naphthylalanine, 2-naphthylalanine, tryptophan, β-2-thienylalanine, homophenylalanine, β-3-pyridylalanine, α-aminobutyric acid, norvaline, norleucine, leucine, and cyclohexylalanine;

D is the L-stereoisomer of a lipophilic aliphatic amino acid;

E is the L-stereoisomer of an aromatic, aliphatic, or alicyclic amino acid;

F is the L-stereoisomer of an aromatic or heteroaromatic amino acid;

G is glycine or D-alanine;

H is L-glutamic acid or L-glutamine;

I is L-glutamine, L-glutamic acid, or L-alanine;

J is a direct bond between land group —NH— or is selected from the group consisting of Z, Z-Leu, Z-Leu-Gln, Z-Leu-Gln-Glu (SEQ ID NO:2), Z-Leu-Gln-Glu-Lys (SEQ ID NO:3), Z-Leu-Gln-Glu-Lys-Glu (SEQ ID NO:4), Z-Leu-Gln-Glu-Lys-Glu-Arg (SEQ ID NO:5), Z-Leu-Gln-Glu-Lys-Glu-Arg-Asn (SEQ ID NO:6), Z-Leu-Gln-Glu-Lys-Glu-Arg-Asn-Lys (SEQ ID NO:7), and Z-Leu-Gln-Glu-Lys-Glu-Arg-Asn-Lys-Gly (SEQ ID NO:8), wherein Z is selected from the group consisting of arginine, D-arginine, D-homoarginine, D-lysine, D-ornithine, D-2,4-diaminobutyric acid, D-glutamine, D-asparagine, and D-alanine;

$R_1$ and $R_2$ are independently hydrogen or lower-alkyl;

$R_3$ is cycloalkyl or aryl which may be unsubstituted or substituted with one or more substituents selected from the group consisting of halogen, hydroxy, and lower-alkoxy;

$R_4$ is selected from the group consisting of —$CH_2CONH_2$, aminoalkyl groups containing from 1 to 3 carbon atoms, and guanidinoalkyl groups containing 2 or 3 carbon atoms;

$R_5$ is —COOH or —$CONH_2$; and the symbol * represents an asymmetric carbon atom which may be in the D or L configuration, and each lower-alkyl group contains from 1 to 4 carbon atoms, with the proviso that $R_4$ is —$CH_2CONH_2$ only when J is Z-Leu or Z-Leu-Gln-Glu-Lys-Glu-Arg-Asn-Lys-Gly (SEQ ID NO:8).

* * * * *

SEQUENCE LISTING ( 1 ) GENERAL INFORMATION:

( i i i ) NUMBER OF SEQUENCES: 154

( 2 ) INFORMATION FOR SEQ ID NO:1:

( i ) SEQUENCE CHARACTERISTICS:
        ( A ) LENGTH: 22 amino acids

```
          ( B ) TYPE: amino acid
          ( C ) STRANDEDNESS: unknown
          ( D ) TOPOLOGY: unknown ( i i ) MOLECULE TYPE: peptide ( x i ) SEQUENCE DESCRIPTION: SEQ ID NO:1:

Phe  Val  Pro  Ile  Phe  Thr  Tyr  Gly  Glu  Leu  Gln  Arg  Met  Gln  Glu  Lys
  1                    5                        10                       15

Glu  Arg  Asn  Lys  Gly  Gln
                 20
```

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:2:

```
  Xaa  Leu  Gln  Glu
  1
```

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:3:

```
  Xaa  Leu  Gln  Glu  Lys
  1                    5
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:4:

```
  Xaa  Leu  Gln  Glu  Lys  Glu
  1                    5
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:5:

```
  Xaa  Leu  Gln  Glu  Lys  Glu  Arg
  1                    5
```

(2) INFORMATION FOR SEQ ID NO:6:

(i) SEQUENCE CHARACTERISTICS:
       (A) LENGTH: 8 amino acids
       (B) TYPE: amino acid
       (C) STRANDEDNESS: unknown
       (D) TOPOLOGY: unknown (ii) MOLECULE TYPE: peptide (xi) SEQUENCE DESCRIPTION: SEQ ID NO:6:

Xaa  Leu  Gln  Glu  Lys  Glu  Arg  Asn
   1                   5

(2) INFORMATION FOR SEQ ID NO:7:

(i) SEQUENCE CHARACTERISTICS:
       (A) LENGTH: 9 amino acids
       (B) TYPE: amino acid
       (C) STRANDEDNESS: unknown
       (D) TOPOLOGY: unknown (ii) MOLECULE TYPE: peptide (xi) SEQUENCE DESCRIPTION: SEQ ID NO:7:

Xaa  Leu  Gln  Glu  Lys  Glu  Arg  Asn  Lys
   1                   5

(2) INFORMATION FOR SEQ ID NO:8:

(i) SEQUENCE CHARACTERISTICS:
       (A) LENGTH: 10 amino acids
       (B) TYPE: amino acid
       (C) STRANDEDNESS: unknown
       (D) TOPOLOGY: unknown (ii) MOLECULE TYPE: peptide (xi) SEQUENCE DESCRIPTION: SEQ ID NO:8:

Xaa  Leu  Gln  Glu  Lys  Glu  Arg  Asn  Lys  Gly
   1                   5                        10

(2) INFORMATION FOR SEQ ID NO:9:

(i) SEQUENCE CHARACTERISTICS:
       (A) LENGTH: 21 amino acids
       (B) TYPE: amino acid
       (C) STRANDEDNESS: unknown
       (D) TOPOLOGY: unknown (ii) MOLECULE TYPE: peptide (xi) SEQUENCE DESCRIPTION: SEQ ID NO:9:

Phe  Val  Phe  Ile  Phe  Thr  Tyr  Gly  Glu  Leu  Gln  Arg  Leu  Gln  Lys  Glu
   1                   5                        10                       15

Arg  Asn  Lys  Gly  Gln
                   20

(2) INFORMATION FOR SEQ ID NO:10:

(i) SEQUENCE CHARACTERISTICS:
       (A) LENGTH: 21 amino acids
       (B) TYPE: amino acid
       (C) STRANDEDNESS: unknown
       (D) TOPOLOGY: unknown (ii) MOLECULE TYPE: peptide (xi) SEQUENCE DESCRIPTION: SEQ ID NO:10:

```
Phe  Val  Phe  Ile  Phe  Thr  Tyr  Gly  Glu  Leu  Gln  Arg  Leu  Gln  Lys  Glu
1              5                        10                       15

Arg  Asn  Lys  Gly  Gln
               20
```

( 2 ) INFORMATION FOR SEQ ID NO:11:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:11:

```
Phe  Val  Xaa  Ile  Phe  Thr  Tyr  Gly  Glu  Leu  Gln  Arg  Leu  Gln  Lys  Glu
1              5                        10                       15

Arg  Asn  Lys  Gly  Gln
               20
```

( 2 ) INFORMATION FOR SEQ ID NO:12:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:12:

```
Phe  Val  Xaa  Ile  Phe  Thr  Tyr  Gly  Glu  Leu  Gln  Arg  Leu  Gln  Lys  Glu
1              5                        10                       15

Arg  Asn  Lys  Gly  Gln
               20
```

( 2 ) INFORMATION FOR SEQ ID NO:13:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:13:

```
Phe  Val  Phe  Ile  Phe  Thr  Tyr  Gly  Glu  Leu  Gln  Arg
1              5                        10
```

( 2 ) INFORMATION FOR SEQ ID NO:14:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:14:

```
Phe  Val  Phe  Ile  Phe  Thr  Tyr  Gly  Glu  Leu  Gln  Arg  Leu  Gln
1              5                        10
```

( 2 ) INFORMATION FOR SEQ ID NO:15:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:15:

Phe Val Phe Ile Phe Thr Tyr Gly Glu Leu Gln Arg Leu Gln
1               5                   10

( 2 ) INFORMATION FOR SEQ ID NO:16:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:16:

Phe Val Phe Ile Phe Thr Tyr Gly Glu Leu Gln Arg Leu Gln
1               5                   10

( 2 ) INFORMATION FOR SEQ ID NO:17:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:17:

Phe Val Xaa Ile Phe Thr Tyr Gly Glu Leu Gln Arg Leu Gln
1               5                   10

( 2 ) INFORMATION FOR SEQ ID NO:18:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:18:

Phe Val Leu Ile Phe Thr Tyr Gly Glu Leu Gln Arg Leu Gln
1               5                   10

( 2 ) INFORMATION FOR SEQ ID NO:19:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:19:

Phe Val Xaa Ile Phe Thr Tyr Gly Glu Leu Gln Arg Leu Gln
1               5                   10

( 2 ) INFORMATION FOR SEQ ID NO:20:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:20:

Phe Val Xaa Ile Phe Thr Tyr Gly Glu Leu Gln Arg Leu Gln
1               5                   10

( 2 ) INFORMATION FOR SEQ ID NO:21:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:21:

Phe Val Xaa Ile Phe Thr Tyr Gly Glu Leu Gln Arg Leu Gln
1               5                   10

( 2 ) INFORMATION FOR SEQ ID NO:22:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:22:

Phe Val Xaa Ile Phe Thr Tyr Gly Glu Leu Gln Arg Leu Gln
1               5                   10

( 2 ) INFORMATION FOR SEQ ID NO:23:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:23:

Phe Val Phe Leu Phe Thr Tyr Gly Glu Leu Gln Arg Leu Gln
1               5                   10

( 2 ) INFORMATION FOR SEQ ID NO:24:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:24:

Phe Val Phe Ile Xaa Thr Tyr Gly Glu Leu Gln Arg Leu Gln
1               5                   10

( 2 ) INFORMATION FOR SEQ ID NO:25:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:25:

```
Phe Val Phe Ile Ala Thr Tyr Gly Glu Leu Gln Arg Leu Gln
1               5                   10
```

( 2 ) INFORMATION FOR SEQ ID NO:26:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:26:

```
Phe Val Phe Ile Phe Thr Phe Gly Glu Leu Gln Arg Leu Gln
1               5                   10
```

( 2 ) INFORMATION FOR SEQ ID NO:27:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:27:

```
Phe Val Phe Ile Phe Thr Tyr Xaa Glu Leu Gln Arg Leu Gln
1               5                   10
```

( 2 ) INFORMATION FOR SEQ ID NO:28:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:28:

```
Phe Val Phe Ile Phe Thr Tyr Gly Gln Leu Gln Arg Leu Gln
1               5                   10
```

( 2 ) INFORMATION FOR SEQ ID NO:29:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:29:

```
Phe Val Phe Ile Phe Thr Tyr Gly Glu Leu Ala Arg Leu Gln
1               5                   10
```

( 2 ) INFORMATION FOR SEQ ID NO:30:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:30:

```
Phe  Leu  Phe  Ile  Phe  Thr  Tyr  Gly  Glu  Leu  Gln  Arg  Leu  Gln
1                   5                        10
```

( 2 ) INFORMATION FOR SEQ ID NO:31:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:31:

```
Phe  Val  Phe  Ile  Phe  Thr  Tyr  Gly  Glu  Leu  Gln  Arg  Leu  Gln
1                   5                        10
```

( 2 ) INFORMATION FOR SEQ ID NO:32:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:32:

```
Phe  Val  Phe  Ile  Phe  Thr  Tyr  Gly  Glu  Leu  Gln  Arg  Leu  Gln
1                   5                        10
```

( 2 ) INFORMATION FOR SEQ ID NO:33:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:33:

```
Phe  Val  Phe  Ile  Phe  Thr  Tyr  Gly  Glu  Leu  Gln  Arg  Leu  Gln
1                   5                        10
```

( 2 ) INFORMATION FOR SEQ ID NO:34:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:34:

```
Phe  Val  Xaa  Ile  Phe  Thr  Tyr  Gly  Glu  Leu  Gln  Arg  Leu  Gln
1                   5                        10
```

( 2 ) INFORMATION FOR SEQ ID NO:35:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:35:

```
Phe Val Leu Ile Phe Thr Tyr Gly Glu Leu Gln Arg Leu Gln
 1               5                   10
```

( 2 ) INFORMATION FOR SEQ ID NO:36:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:36:

```
Phe Val Xaa Ile Phe Thr Tyr Gly Glu Leu Gln Arg Leu Gln
 1               5                   10
```

( 2 ) INFORMATION FOR SEQ ID NO:37:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:37:

```
Phe Val Xaa Ile Phe Thr Tyr Gly Glu Leu Gln Arg Leu Gln
 1               5                   10
```

( 2 ) INFORMATION FOR SEQ ID NO:38:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:38:

```
Phe Val Xaa Ile Phe Thr Tyr Gly Glu Leu Gln Arg Leu Gln
 1               5                   10
```

( 2 ) INFORMATION FOR SEQ ID NO:39:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:39:

```
Phe Val Xaa Ile Phe Thr Tyr Gly Glu Leu Gln Arg Leu Gln
```

(2) INFORMATION FOR SEQ ID NO:40:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:40:

```
Phe Val Phe Leu Phe Thr Tyr Gly Glu Leu Gln Arg Leu Gln
 1               5                   10
```

(2) INFORMATION FOR SEQ ID NO:41:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:41:

```
Phe Val Phe Ile Xaa Thr Tyr Gly Glu Leu Gln Arg Leu Gln
 1               5                   10
```

(2) INFORMATION FOR SEQ ID NO:42:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:42:

```
Phe Val Phe Ile Ala Thr Tyr Gly Glu Leu Gln Arg Leu Gln
 1               5                   10
```

(2) INFORMATION FOR SEQ ID NO:43:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:43:

```
Phe Val Phe Ile Phe Thr Phe Gly Glu Leu Gln Arg Leu Gln
 1               5                   10
```

(2) INFORMATION FOR SEQ ID NO:44:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:44:

```
        Phe  Val  Phe  Ile  Phe  Thr  Tyr  Xaa  Glu  Leu  Gln  Arg  Leu  Gln
        1                  5                      10
```

( 2 ) INFORMATION FOR SEQ ID NO:45:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:45:

```
        Phe  Val  Phe  Ile  Phe  Thr  Tyr  Gly  Gln  Leu  Gln  Arg  Leu  Gln
        1                  5                      10
```

( 2 ) INFORMATION FOR SEQ ID NO:46:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:46:

```
        Phe  Val  Phe  Ile  Phe  Thr  Tyr  Gly  Glu  Leu  Ala  Arg  Leu  Gln
        1                  5                      10
```

( 2 ) INFORMATION FOR SEQ ID NO:47:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:47:

```
        Phe  Leu  Phe  Ile  Phe  Thr  Tyr  Gly  Glu  Leu  Gln  Arg  Leu  Gln
        1                  5                      10
```

( 2 ) INFORMATION FOR SEQ ID NO:48:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:48:

```
        Phe  Val  Phe  Ile  Phe  Thr  Tyr  Gly  Glu  Leu  Gln  Arg  Leu  Lys
        1                  5                      10
```

( 2 ) INFORMATION FOR SEQ ID NO:49:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:49:

```
Xaa  Val  Phe  Ile  Phe  Thr  Tyr  Gly  Glu  Leu  Gln  Arg  Leu  Gln
 1                  5                        10
```

( 2 ) INFORMATION FOR SEQ ID NO:50:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:50:

```
Xaa  Val  Phe  Ile  Phe  Thr  Tyr  Gly  Glu  Leu  Gln  Arg  Leu  Gln
 1                  5                        10
```

( 2 ) INFORMATION FOR SEQ ID NO:51:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:51:

```
Phe  Val  Xaa  Ile  Phe  Thr  Tyr  Gly  Glu  Leu  Gln  Arg  Leu  Gln
 1                  5                        10
```

( 2 ) INFORMATION FOR SEQ ID NO:52:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:52:

```
Xaa  Val  Phe  Ile  Phe  Thr  Tyr  Gly  Glu  Leu  Gln  Arg  Leu  Gln
 1                  5                        10
```

( 2 ) INFORMATION FOR SEQ ID NO:53:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:53:

```
Xaa  Val  Phe  Ile  Phe  Thr  Tyr  Gly  Glu  Leu  Gln  Arg  Leu  Gln
 1                  5                        10
```

( 2 ) INFORMATION FOR SEQ ID NO:54:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide (xi) SEQUENCE DESCRIPTION: SEQ ID NO:54:

Phe Val Xaa Ile Phe Thr Tyr Gly Glu Leu Gln Arg Leu Gln
1               5                   10

(2) INFORMATION FOR SEQ ID NO:55:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:55:

Phe Val Phe Ile Phe Thr Tyr Gly Glu Leu Gln Arg Leu Xaa
1               5                   10

(2) INFORMATION FOR SEQ ID NO:56:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:56:

Phe Val Xaa Ile Phe Thr Tyr Gly Glu Leu Gln Arg
1               5                   10

(2) INFORMATION FOR SEQ ID NO:57:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:57:

Phe Val Xaa Ile Phe Thr Tyr Gly Glu Leu Gln Arg Leu Gln
1               5                   10

(2) INFORMATION FOR SEQ ID NO:58:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:58:

Phe Val Xaa Ile Phe Thr Tyr Gly Glu Leu Gln Arg Leu Gln
1               5                   10

(2) INFORMATION FOR SEQ ID NO:59:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide ( x i ) SEQUENCE DESCRIPTION: SEQ ID NO:59:

Phe Val Xaa Ile Phe Thr Tyr Gly Glu Leu Gln Arg Leu Gln
1               5                   10

( 2 ) INFORMATION FOR SEQ ID NO:60:

( i ) SEQUENCE CHARACTERISTICS:
      ( A ) LENGTH: 14 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:60:

Phe Val Xaa Leu Phe Thr Tyr Gly Glu Leu Gln Arg Leu Gln
1               5                   10

( 2 ) INFORMATION FOR SEQ ID NO:61:

( i ) SEQUENCE CHARACTERISTICS:
      ( A ) LENGTH: 14 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:61:

Phe Val Xaa Ile Xaa Thr Tyr Gly Glu Leu Gln Arg Leu Gln
1               5                   10

( 2 ) INFORMATION FOR SEQ ID NO:62:

( i ) SEQUENCE CHARACTERISTICS:
      ( A ) LENGTH: 14 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:62:

Phe Val Xaa Ile Ala Thr Tyr Gly Glu Leu Gln Arg Leu Gln
1               5                   10

( 2 ) INFORMATION FOR SEQ ID NO:63:

( i ) SEQUENCE CHARACTERISTICS:
      ( A ) LENGTH: 14 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:63:

Phe Val Xaa Ile Phe Thr Phe Gly Glu Leu Gln Arg Leu Gln
1               5                   10

( 2 ) INFORMATION FOR SEQ ID NO:64:

( i ) SEQUENCE CHARACTERISTICS:
      ( A ) LENGTH: 14 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:64:

```
Phe Val Xaa Ile Phe Thr Tyr Xaa Glu Leu Gln Arg Leu Gln
1               5                   10
```

( 2 ) INFORMATION FOR SEQ ID NO:65:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:65:

```
Phe Val Xaa Ile Phe Thr Tyr Gly Gln Leu Gln Arg Leu Gln
1               5                   10
```

( 2 ) INFORMATION FOR SEQ ID NO:66:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:66:

```
Phe Val Xaa Ile Phe Thr Tyr Gly Glu Leu Ala Arg Leu Gln
1               5                   10
```

( 2 ) INFORMATION FOR SEQ ID NO:67:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:67:

```
Phe Leu Xaa Ile Phe Thr Tyr Gly Glu Leu Gln Arg Leu Gln
1               5                   10
```

( 2 ) INFORMATION FOR SEQ ID NO:68:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:68:

```
Phe Val Xaa Ile Phe Thr Tyr Gly Glu Leu Gln Arg Leu Gln
1               5                   10
```

( 2 ) INFORMATION FOR SEQ ID NO:69:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown (i i) MOLECULE TYPE: peptide (x i) SEQUENCE DESCRIPTION: SEQ ID NO:69:

Phe Val Xaa Ile Phe Thr Tyr Gly Glu Leu Gln Arg Leu Gln
1               5                   10

(2) INFORMATION FOR SEQ ID NO:70:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:70:

Phe Val Xaa Ile Phe Thr Tyr Gly Glu Leu Gln Arg Leu Gln
1               5                   10

(2) INFORMATION FOR SEQ ID NO:71:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:71:

Phe Val Xaa Leu Phe Thr Tyr Gly Glu Leu Gln Arg Leu Gln
1               5                   10

(2) INFORMATION FOR SEQ ID NO:72:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:72:

Phe Val Xaa Ile Xaa Thr Tyr Gly Glu Leu Gln Arg Leu Gln
1               5                   10

(2) INFORMATION FOR SEQ ID NO:73:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (i i) MOLECULE TYPE: peptide (x i) SEQUENCE DESCRIPTION: SEQ ID NO:73:

Phe Val Xaa Ile Ala Thr Tyr Gly Glu Leu Gln Arg Leu Gln
1               5                   10

(2) INFORMATION FOR SEQ ID NO:74:

(i) SEQUENCE CHARACTERISTICS:
        (A) LENGTH: 14 amino acids
        (B) TYPE: amino acid
        (C) STRANDEDNESS: unknown (D) TOPOLOGY: unknown (ii) MOLECULE TYPE: peptide (xi) SEQUENCE DESCRIPTION: SEQ ID NO:74:

```
Phe Val Xaa Ile Phe Thr Phe Gly Glu Leu Gln Arg Leu Gln
1               5                   10
```

(2) INFORMATION FOR SEQ ID NO:75:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:75:

```
Phe Val Xaa Ile Phe Thr Tyr Xaa Glu Leu Gln Arg Leu Gln
1               5                   10
```

(2) INFORMATION FOR SEQ ID NO:76:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:76:

```
Phe Val Xaa Ile Phe Thr Tyr Gly Gln Leu Gln Arg Leu Gln
1               5                   10
```

(2) INFORMATION FOR SEQ ID NO:77:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:77:

```
Phe Val Xaa Ile Phe Thr Tyr Gly Glu Leu Ala Arg Leu Gln
1               5                   10
```

(2) INFORMATION FOR SEQ ID NO:78:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:78:

```
Phe Leu Xaa Ile Phe Thr Tyr Gly Glu Leu Gln Arg Leu Gln
1               5                   10
```

(2) INFORMATION FOR SEQ ID NO:79:

(i) SEQUENCE CHARACTERISTICS:
        (A) LENGTH: 14 amino acids
        (B) TYPE: amino acid (C) STRANDEDNESS: unknown
(D) TOPOLOGY: unknown (i i) MOLECULE TYPE: peptide (x i) SEQUENCE DESCRIPTION: SEQ ID NO:79:

Phe Val Xaa Ile Phe Thr Tyr Gly Glu Leu Gln Arg Leu Lys
1               5                   10

(2) INFORMATION FOR SEQ ID NO:80:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (i i) MOLECULE TYPE: peptide (x i) SEQUENCE DESCRIPTION: SEQ ID NO:80:

Xaa Val Xaa Ile Phe Thr Tyr Gly Glu Leu Gln Arg Leu Gln
1               5                   10

(2) INFORMATION FOR SEQ ID NO:81:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (i i) MOLECULE TYPE: peptide (x i) SEQUENCE DESCRIPTION: SEQ ID NO:81:

Xaa Val Xaa Ile Phe Thr Tyr Gly Glu Leu Gln Arg Leu Gln
1               5                   10

(2) INFORMATION FOR SEQ ID NO:82:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (i i) MOLECULE TYPE: peptide (x i) SEQUENCE DESCRIPTION: SEQ ID NO:82:

Phe Val Xaa Ile Phe Thr Tyr Gly Glu Leu Gln Arg Leu Gln
1               5                   10

(2) INFORMATION FOR SEQ ID NO:83:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (i i) MOLECULE TYPE: peptide (x i) SEQUENCE DESCRIPTION: SEQ ID NO:83:

Xaa Val Xaa Ile Phe Thr Tyr Gly Glu Leu Gln Arg Leu Gln
1               5                   10

(2) INFORMATION FOR SEQ ID NO:84:

(i) SEQUENCE CHARACTERISTICS:
    (A) LENGTH: 14 amino acids (B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:84:

Xaa Val Xaa Ile Phe Thr Tyr Gly Glu Leu Gln Arg Leu Gln
1               5                   10

(2) INFORMATION FOR SEQ ID NO:85:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:85:

Phe Val Xaa Ile Phe Thr Tyr Gly Glu Leu Gln Arg Leu Gln
1               5                   10

(2) INFORMATION FOR SEQ ID NO:86:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:86:

Phe Val Xaa Ile Phe Thr Tyr Gly Glu Leu Gln Arg Leu Xaa
1               5                   10

(2) INFORMATION FOR SEQ ID NO:87:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:87:

Phe Val Xaa Ile Phe Thr Tyr Gly Glu Leu Gln Arg Leu Xaa
1               5                   10

(2) INFORMATION FOR SEQ ID NO:88:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:88:

Phe Val Xaa Ile Phe Thr Tyr Gly Glu Leu Gln Arg Leu Xaa
1               5                   10

(2) INFORMATION FOR SEQ ID NO:89:

(i) SEQUENCE CHARACTERISTICS:

(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:89:

Phe Val Phe Ile Phe Thr Tyr Gly Glu Leu Gln Arg Leu Xaa
1               5                   10

(2) INFORMATION FOR SEQ ID NO:90:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:90:

Phe Val Phe Ile Phe Thr Tyr Gly Glu Leu Gln Arg Leu Xaa
1               5                   10

(2) INFORMATION FOR SEQ ID NO:91:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:91:

Phe Val Xaa Ile Phe Thr Tyr Gly Glu Leu Gln Xaa Leu Gln
1               5                   10

(2) INFORMATION FOR SEQ ID NO:92:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:92:

Phe Val Xaa Ile Phe Thr Tyr Gly Glu Leu Gln Xaa Leu Gln
1               5                   10

(2) INFORMATION FOR SEQ ID NO:93:

(i) SEQUENCE CHARACTERISTICS:
(A) LENGTH: 14 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:93:

Phe Val Phe Ile Phe Thr Tyr Gly Glu Leu Gln Xaa Leu Gln
1               5                   10

(2) INFORMATION FOR SEQ ID NO:94:

( i ) SEQUENCE CHARACTERISTICS:
  ( A ) LENGTH: 14 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:94:

Phe Val Phe Ile Phe Thr Tyr Gly Glu Leu Gln Xaa Leu Gln
1               5                   10

( 2 ) INFORMATION FOR SEQ ID NO:95:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:95:

Phe Val Xaa Ile Phe Thr Tyr Gly Glu Leu Gln Arg Leu Lys
1               5                   10

( 2 ) INFORMATION FOR SEQ ID NO:96:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:96:

Phe Val Phe Ile Phe Thr Tyr Gly Glu Leu Gln Arg Leu Lys
1               5                   10

( 2 ) INFORMATION FOR SEQ ID NO:97:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:97:

Phe Val Phe Ile Phe Thr Tyr Gly Glu Leu Gln Arg Leu Lys
1               5                   10

( 2 ) INFORMATION FOR SEQ ID NO:98:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:98:

Phe Val Phe Ile Phe Thr Tyr Gly Glu Leu Gln Arg Leu Lys
1               5                   10

( 2 ) INFORMATION FOR SEQ ID NO:99:

( i ) SEQUENCE CHARACTERISTICS:
  ( A ) LENGTH: 14 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:99:

Phe Val Xaa Ile Phe Thr Tyr Gly Glu Leu Gln Xaa Leu Lys
1               5                   10

( 2 ) INFORMATION FOR SEQ ID NO:100:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:100:

Phe Val Xaa Ile Phe Thr Tyr Gly Glu Leu Gln Xaa Leu Lys
1               5                   10

( 2 ) INFORMATION FOR SEQ ID NO:101:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:101:

Phe Val Phe Ile Phe Thr Tyr Gly Glu Leu Gln Xaa Leu Lys
1               5                   10

( 2 ) INFORMATION FOR SEQ ID NO:102:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:102:

Phe Val Phe Ile Phe Thr Tyr Gly Glu Leu Gln Xaa Leu Lys
1               5                   10

( 2 ) INFORMATION FOR SEQ ID NO:103:

( i ) SEQUENCE CHARACTERISTICS:
    ( A ) LENGTH: 14 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:103:

Phe Val Xaa Ile Phe Thr Tyr Gly Glu Leu Gln Arg Leu Xaa
1               5                   10

( 2 ) INFORMATION FOR SEQ ID NO:104:

( i ) SEQUENCE CHARACTERISTICS:
      ( A ) LENGTH: 14 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:104:

```
Phe  Val  Xaa  Ile  Phe  Thr  Tyr  Gly  Glu  Leu  Gln  Arg  Leu  Xaa
 1              5                        10
```

( 2 ) INFORMATION FOR SEQ ID NO:105:

( i ) SEQUENCE CHARACTERISTICS:
      ( A ) LENGTH: 14 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:105:

```
Phe  Val  Phe  Ile  Phe  Thr  Tyr  Gly  Glu  Leu  Gln  Arg  Leu  Xaa
 1              5                        10
```

( 2 ) INFORMATION FOR SEQ ID NO:106:

( i ) SEQUENCE CHARACTERISTICS:
      ( A ) LENGTH: 14 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:106:

```
Phe  Val  Phe  Ile  Phe  Thr  Tyr  Gly  Glu  Leu  Gln  Arg  Leu  Xaa
 1              5                        10
```

( 2 ) INFORMATION FOR SEQ ID NO:107:

( i ) SEQUENCE CHARACTERISTICS:
      ( A ) LENGTH: 14 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:107:

```
Phe  Val  Xaa  Ile  Phe  Thr  Tyr  Gly  Glu  Leu  Gln  Xaa  Leu  Xaa
 1              5                        10
```

( 2 ) INFORMATION FOR SEQ ID NO:108:

( i ) SEQUENCE CHARACTERISTICS:
      ( A ) LENGTH: 14 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:108:

```
Phe  Val  Xaa  Ile  Phe  Thr  Tyr  Gly  Glu  Leu  Gln  Xaa  Leu  Xaa
 1              5                        10
```

( 2 ) INFORMATION FOR SEQ ID NO:109:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:109:

```
Phe  Val  Phe  Ile  Phe  Thr  Tyr  Gly  Glu  Leu  Gln  Xaa  Leu  Xaa
1                  5                        10
```

( 2 ) INFORMATION FOR SEQ ID NO:110:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:110:

```
Phe  Val  Phe  Ile  Phe  Thr  Tyr  Gly  Glu  Leu  Gln  Xaa  Leu  Xaa
1                  5                        10
```

( 2 ) INFORMATION FOR SEQ ID NO:111:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:111:

```
Phe  Val  Xaa  Ile  Phe  Thr  Tyr  Gly  Glu  Leu  Gln  Xaa  Leu  Xaa
1                  5                        10
```

( 2 ) INFORMATION FOR SEQ ID NO:112:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:112:

```
Phe  Val  Xaa  Ile  Phe  Thr  Tyr  Gly  Glu  Leu  Gln  Xaa  Leu  Xaa
1                  5                        10
```

( 2 ) INFORMATION FOR SEQ ID NO:113:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:113:

```
Phe  Val  Phe  Ile  Phe  Thr  Tyr  Gly  Glu  Leu  Gln  Xaa  Leu  Xaa
1                  5                        10
```

( 2 ) INFORMATION FOR SEQ ID NO:114:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:114:

```
Phe  Val  Phe  Ile  Phe  Thr  Tyr  Gly  Glu  Leu  Gln  Xaa  Leu  Xaa
1                   5                        10
```

( 2 ) INFORMATION FOR SEQ ID NO:115:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:115:

```
Phe  Val  Xaa  Ile  Phe  Thr  Tyr  Gly  Glu  Leu  Ala  Arg  Leu  Gln
1                   5                        10
```

( 2 ) INFORMATION FOR SEQ ID NO:116:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:116:

```
Phe  Val  Xaa  Ile  Phe  Thr  Tyr  Gly  Glu  Leu  Ala  Arg  Leu  Gln
1                   5                        10
```

( 2 ) INFORMATION FOR SEQ ID NO:117:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:117:

```
Phe  Val  Phe  Ile  Phe  Thr  Tyr  Gly  Glu  Leu  Ala  Arg  Leu  Gln
1                   5                        10
```

( 2 ) INFORMATION FOR SEQ ID NO:118:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:118:

```
Phe  Val  Phe  Ile  Phe  Thr  Tyr  Gly  Glu  Leu  Ala  Arg  Leu  Gln
```

(2) INFORMATION FOR SEQ ID NO:119:

(i) SEQUENCE CHARACTERISTICS:
      (A) LENGTH: 14 amino acids
      (B) TYPE: amino acid
      (C) STRANDEDNESS: unknown
      (D) TOPOLOGY: unknown (ii) MOLECULE TYPE: peptide (xi) SEQUENCE DESCRIPTION: SEQ ID NO:119:

Phe  Val  Xaa  Ile  Phe  Thr  Tyr  Gly  Glu  Leu  Ala  Arg  Leu  Xaa
   1                  5                          10

(2) INFORMATION FOR SEQ ID NO:120:

(i) SEQUENCE CHARACTERISTICS:
      (A) LENGTH: 14 amino acids
      (B) TYPE: amino acid
      (C) STRANDEDNESS: unknown
      (D) TOPOLOGY: unknown (ii) MOLECULE TYPE: peptide (xi) SEQUENCE DESCRIPTION: SEQ ID NO:120:

Phe  Val  Xaa  Ile  Phe  Thr  Tyr  Gly  Glu  Leu  Ala  Arg  Leu  Xaa
   1                  5                          10

(2) INFORMATION FOR SEQ ID NO:121:

(i) SEQUENCE CHARACTERISTICS:
      (A) LENGTH: 14 amino acids
      (B) TYPE: amino acid
      (C) STRANDEDNESS: unknown
      (D) TOPOLOGY: unknown (ii) MOLECULE TYPE: peptide (xi) SEQUENCE DESCRIPTION: SEQ ID NO:121:

Phe  Val  Phe  Ile  Phe  Thr  Tyr  Gly  Glu  Leu  Ala  Arg  Leu  Xaa
   1                  5                          10

(2) INFORMATION FOR SEQ ID NO:122:

(i) SEQUENCE CHARACTERISTICS:
      (A) LENGTH: 14 amino acids
      (B) TYPE: amino acid
      (C) STRANDEDNESS: unknown
      (D) TOPOLOGY: unknown (ii) MOLECULE TYPE: peptide (xi) SEQUENCE DESCRIPTION: SEQ ID NO:122:

Phe  Val  Phe  Ile  Phe  Thr  Tyr  Gly  Glu  Leu  Ala  Arg  Leu  Xaa
   1                  5                          10

(2) INFORMATION FOR SEQ ID NO:123:

(i) SEQUENCE CHARACTERISTICS:
      (A) LENGTH: 14 amino acids
      (B) TYPE: amino acid
      (C) STRANDEDNESS: unknown
      (D) TOPOLOGY: unknown (ii) MOLECULE TYPE: peptide (xi) SEQUENCE DESCRIPTION: SEQ ID NO:123:

```
Phe Val Xaa Ile Phe Thr Tyr Gly Glu Leu Ala Xaa Leu Gln
1               5                   10
```

( 2 ) INFORMATION FOR SEQ ID NO:124:

( i ) SEQUENCE CHARACTERISTICS:
       ( A ) LENGTH: 14 amino acids
       ( B ) TYPE: amino acid
       ( C ) STRANDEDNESS: unknown
       ( D ) TOPOLOGY: unknown ( i i ) MOLECULE TYPE: peptide ( x i ) SEQUENCE DESCRIPTION: SEQ ID NO:124:

```
Phe Val Xaa Ile Phe Thr Tyr Gly Glu Leu Ala Xaa Leu Gln
1               5                   10
```

( 2 ) INFORMATION FOR SEQ ID NO:125:

( i ) SEQUENCE CHARACTERISTICS:
       ( A ) LENGTH: 14 amino acids
       ( B ) TYPE: amino acid
       ( C ) STRANDEDNESS: unknown
       ( D ) TOPOLOGY: unknown ( i i ) MOLECULE TYPE: peptide ( x i ) SEQUENCE DESCRIPTION: SEQ ID NO:125:

```
Phe Val Phe Ile Phe Thr Tyr Gly Glu Leu Ala Xaa Leu Gln
1               5                   10
```

( 2 ) INFORMATION FOR SEQ ID NO:126:

( i ) SEQUENCE CHARACTERISTICS:
       ( A ) LENGTH: 14 amino acids
       ( B ) TYPE: amino acid
       ( C ) STRANDEDNESS: unknown
       ( D ) TOPOLOGY: unknown ( i i ) MOLECULE TYPE: peptide ( x i ) SEQUENCE DESCRIPTION: SEQ ID NO:126:

```
Phe Val Phe Ile Phe Thr Tyr Gly Glu Leu Ala Xaa Leu Gln
1               5                   10
```

( 2 ) INFORMATION FOR SEQ ID NO:127:

( i ) SEQUENCE CHARACTERISTICS:
       ( A ) LENGTH: 14 amino acids
       ( B ) TYPE: amino acid
       ( C ) STRANDEDNESS: unknown
       ( D ) TOPOLOGY: unknown ( i i ) MOLECULE TYPE: peptide ( x i ) SEQUENCE DESCRIPTION: SEQ ID NO:127:

```
Phe Val Xaa Ile Phe Thr Tyr Gly Glu Leu Ala Xaa Leu Xaa
1               5                   10
```

( 2 ) INFORMATION FOR SEQ ID NO:128:

( i ) SEQUENCE CHARACTERISTICS:
       ( A ) LENGTH: 14 amino acids
       ( B ) TYPE: amino acid
       ( C ) STRANDEDNESS: unknown
       ( D ) TOPOLOGY: unknown ( i i ) MOLECULE TYPE: peptide ( x i ) SEQUENCE DESCRIPTION: SEQ ID NO:128:

```
        Phe  Val  Xaa  Ile  Phe  Thr  Tyr  Gly  Glu  Leu  Ala  Xaa  Leu  Xaa
        1                   5                        10
```

( 2 ) INFORMATION FOR SEQ ID NO:129:

( i ) SEQUENCE CHARACTERISTICS:
         ( A ) LENGTH: 14 amino acids
         ( B ) TYPE: amino acid
         ( C ) STRANDEDNESS: unknown
         ( D ) TOPOLOGY: unknown ( i i ) MOLECULE TYPE: peptide ( x i ) SEQUENCE DESCRIPTION: SEQ ID NO:129:

```
        Phe  Val  Phe  Ile  Phe  Thr  Tyr  Gly  Glu  Leu  Ala  Xaa  Leu  Xaa
        1                   5                        10
```

( 2 ) INFORMATION FOR SEQ ID NO:130:

( i ) SEQUENCE CHARACTERISTICS:
         ( A ) LENGTH: 14 amino acids
         ( B ) TYPE: amino acid
         ( C ) STRANDEDNESS: unknown
         ( D ) TOPOLOGY: unknown ( i i ) MOLECULE TYPE: peptide ( x i ) SEQUENCE DESCRIPTION: SEQ ID NO:130:

```
        Phe  Val  Phe  Ile  Phe  Thr  Tyr  Gly  Glu  Leu  Ala  Xaa  Leu  Xaa
        1                   5                        10
```

( 2 ) INFORMATION FOR SEQ ID NO:131:

( i ) SEQUENCE CHARACTERISTICS:
         ( A ) LENGTH: 14 amino acids
         ( B ) TYPE: amino acid
         ( C ) STRANDEDNESS: unknown
         ( D ) TOPOLOGY: unknown ( i i ) MOLECULE TYPE: peptide ( x i ) SEQUENCE DESCRIPTION: SEQ ID NO:131:

```
        Phe  Val  Xaa  Ile  Phe  Thr  Tyr  Gly  Glu  Leu  Ala  Xaa  Leu  Lys
        1                   5                        10
```

( 2 ) INFORMATION FOR SEQ ID NO:132:

( i ) SEQUENCE CHARACTERISTICS:
         ( A ) LENGTH: 14 amino acids
         ( B ) TYPE: amino acid
         ( C ) STRANDEDNESS: unknown
         ( D ) TOPOLOGY: unknown ( i i ) MOLECULE TYPE: peptide ( x i ) SEQUENCE DESCRIPTION: SEQ ID NO:132:

```
        Phe  Val  Xaa  Ile  Phe  Thr  Tyr  Gly  Glu  Leu  Ala  Xaa  Leu  Lys
        1                   5                        10
```

( 2 ) INFORMATION FOR SEQ ID NO:133:

( i ) SEQUENCE CHARACTERISTICS:
         ( A ) LENGTH: 14 amino acids
         ( B ) TYPE: amino acid
         ( C ) STRANDEDNESS: unknown
         ( D ) TOPOLOGY: unknown ( i i ) MOLECULE TYPE: peptide ( x i ) SEQUENCE DESCRIPTION: SEQ ID NO:133:

Phe Val Phe Ile Phe Thr Tyr Gly Glu Leu Ala Xaa Leu Lys
1               5                           10

( 2 ) INFORMATION FOR SEQ ID NO:134:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:134:

Phe Val Phe Ile Phe Thr Tyr Gly Glu Leu Ala Xaa Leu Lys
1               5                           10

( 2 ) INFORMATION FOR SEQ ID NO:135:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:135:

Phe Val Xaa Ile Phe Thr Tyr Gly Glu Leu Ala Xaa Leu Xaa
1               5                           10

( 2 ) INFORMATION FOR SEQ ID NO:136:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:136:

Phe Val Xaa Ile Phe Thr Tyr Gly Glu Leu Ala Xaa Leu Xaa
1               5                           10

( 2 ) INFORMATION FOR SEQ ID NO:137:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:137:

Phe Val Phe Ile Phe Thr Tyr Gly Glu Leu Ala Xaa Leu Xaa
1               5                           10

( 2 ) INFORMATION FOR SEQ ID NO:138:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:138:

Phe Val Phe Ile Phe Thr Tyr Gly Glu Leu Ala Xaa Leu Xaa
1               5                   10

( 2 ) INFORMATION FOR SEQ ID NO:139:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:139:

Phe Val Xaa Ile Phe Thr Tyr Gly Glu Leu Gln Arg
1               5                   10

( 2 ) INFORMATION FOR SEQ ID NO:140:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:140:

Phe Val Xaa Ile Phe Thr Tyr Gly Glu Leu Gln Arg
1               5                   10

( 2 ) INFORMATION FOR SEQ ID NO:141:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:141:

Phe Val Phe Ile Phe Thr Tyr Gly Glu Leu Gln Arg
1               5                   10

( 2 ) INFORMATION FOR SEQ ID NO:142:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:142:

Phe Val Phe Ile Phe Thr Tyr Gly Glu Leu Gln Arg
1               5                   10

( 2 ) INFORMATION FOR SEQ ID NO:143:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:143:

Phe Val Xaa Ile Phe Thr Tyr Gly Gln Leu Ala Arg
1               5                   10

( 2 ) INFORMATION FOR SEQ ID NO:144:

( i ) SEQUENCE CHARACTERISTICS:
( A ) LENGTH: 12 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:144:

Phe Val Xaa Ile Phe Thr Tyr Gly Gln Leu Ala Arg
1               5                   10

( 2 ) INFORMATION FOR SEQ ID NO:145:

( i ) SEQUENCE CHARACTERISTICS:
( A ) LENGTH: 12 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:145:

Phe Val Phe Ile Phe Thr Tyr Gly Gln Leu Ala Arg
1               5                   10

( 2 ) INFORMATION FOR SEQ ID NO:146:

( i ) SEQUENCE CHARACTERISTICS:
( A ) LENGTH: 12 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:146:

Phe Val Phe Ile Phe Thr Tyr Gly Gln Leu Ala Arg
1               5                   10

( 2 ) INFORMATION FOR SEQ ID NO:147:

( i ) SEQUENCE CHARACTERISTICS:
( A ) LENGTH: 12 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:147:

Phe Val Xaa Ile Phe Thr Tyr Gly Glu Leu Gln Xaa
1               5                   10

( 2 ) INFORMATION FOR SEQ ID NO:148:

( i ) SEQUENCE CHARACTERISTICS:
( A ) LENGTH: 12 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:148:

Phe Val Xaa Ile Phe Thr Tyr Gly Glu Leu Gln Xaa
1               5                       10

( 2 ) INFORMATION FOR SEQ ID NO:149:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:149:

Phe Val Phe Ile Phe Thr Tyr Gly Glu Leu Gln Xaa
1               5                       10

( 2 ) INFORMATION FOR SEQ ID NO:150:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:150:

Phe Val Phe Ile Phe Thr Tyr Gly Glu Leu Gln Xaa
1               5                       10

( 2 ) INFORMATION FOR SEQ ID NO:151:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:151:

Phe Val Xaa Ile Phe Thr Tyr Gly Glu Leu Ala Xaa
1               5                       10

( 2 ) INFORMATION FOR SEQ ID NO:152:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:152:

Phe Val Xaa Ile Phe Thr Tyr Gly Glu Leu Ala Xaa
1               5                       10

( 2 ) INFORMATION FOR SEQ ID NO:153:

( i ) SEQUENCE CHARACTERISTICS:
        ( A ) LENGTH: 12 amino acids
        ( B ) TYPE: amino acid
        ( C ) STRANDEDNESS: unknown -continued (D) TOPOLOGY: unknown (ii) MOLECULE TYPE: peptide (xi) SEQUENCE DESCRIPTION: SEQ ID NO:153:

Phe Val Phe Ile Phe Thr Tyr Gly Glu Leu Ala Xaa
1               5                       10

(2) INFORMATION FOR SEQ ID NO:154:

(i) SEQUENCE CHARACTERISTICS:
(A) LENGTH: 12 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:154:

Phe Val Phe Ile Phe Thr Tyr Gly Glu Leu Ala Xaa
1               5                       10